(12) United States Patent  
Harris

(10) Patent No.: US 9,105,174 B2  
(45) Date of Patent: Aug. 11, 2015

(54) SYSTEM AND METHODS FOR NONVERBALLY COMMUNICATING PATIENT COMFORT DATA

(71) Applicant: Mark Matthew Harris, Bothell, WA (US)

(72) Inventor: Mark Matthew Harris, Bothell, WA (US)

(*) Notice: Subject to any disclaimer, the term of this patent is extended or adjusted under 35 U.S.C. 154(b) by 0 days.

(21) Appl. No.: 14/548,485

(22) Filed: Nov. 20, 2014

(65) Prior Publication Data

US 2015/0145682 A1    May 28, 2015

Related U.S. Application Data

(60) Provisional application No. 61/908,706, filed on Nov. 25, 2013.

(51) Int. Cl.
G08B 21/18 (2006.01)
G06F 19/00 (2011.01)
G06F 3/033 (2013.01)

(52) U.S. Cl.
CPC ............. *G08B 21/18* (2013.01); *G06F 19/363* (2013.01); *G06F 3/033* (2013.01)

(58) Field of Classification Search
None
See application file for complete search history.

(56) References Cited

U.S. PATENT DOCUMENTS

| | | | |
|---|---|---|---|
| 5,653,739 A | | 8/1997 | Maurer et al. |
| 5,720,502 A | * | 2/1998 | Cain .............................. 283/115 |
| 5,873,900 A | | 2/1999 | Maurer et al. |
| 5,984,368 A | * | 11/1999 | Cain .............................. 283/115 |
| 6,529,195 B1 | | 3/2003 | Eberlein |
| 6,551,103 B2 | * | 4/2003 | Gottfried ....................... 433/229 |
| 6,856,315 B2 | | 2/2005 | Eberlein |
| 6,899,687 B2 | | 5/2005 | Hori et al. |
| 8,087,936 B2 | * | 1/2012 | Knable .......................... 434/112 |
| 8,764,650 B2 | | 7/2014 | Schiavenato et al. |
| 2002/0030682 A1 | | 3/2002 | Eberlein |
| 2006/0055544 A1 | * | 3/2006 | Morguelan ................. 340/573.1 |
| 2006/0275739 A1 | * | 12/2006 | Ray ............................... 433/215 |
| 2007/0078878 A1 | * | 4/2007 | Knable ......................... 707/101 |
| 2007/0174079 A1 | | 7/2007 | Kraus |
| 2011/0029325 A1 | | 2/2011 | Georgiev et al. |
| 2011/0066078 A1 | * | 3/2011 | Sarvazyan et al. ............. 600/587 |
| 2012/0316473 A1 | * | 12/2012 | Bonutti et al. ..................... 601/2 |
| 2014/0114375 A1 | * | 4/2014 | Chapa et al. ..................... 607/57 |

\* cited by examiner

*Primary Examiner* — Firmin Backer  
*Assistant Examiner* — Nay Tun

(57) ABSTRACT

Systems and methods for nonverbally communicating patient comfort data are disclosed herein. In some embodiments, the systems and methods may include one or more operations including receiving patient comfort data associated with one or more patients through a patient comfort level input device during a course of a treatment session, transmitting the patient comfort data associated with one or more patients received through the patient comfort level input device, and alerting one or more practitioners of the patient comfort data associated with one or more patients received through the patient comfort level input device. In some embodiments, the systems and methods may include at least one of the additional operations of receiving objective data indicating one or more particular treatment types substantially contemporaneously with a performance of the one or more particular treatment types and automatically generating one or more objective treatment session notes for inclusion within at least one of one or more patient charts and one or more medical records.

15 Claims, 16 Drawing Sheets

SYSTEM AND METHODS FOR NONVERBALLY COMMUNICATING PATIENT COMFORT DATA

CROSS-REFERENCE TO RELATED APPLICATIONS

The present application claims the benefit of U.S. Provisional Patent Application No. 61/908,706 filed Nov. 25, 2013, entitled "Apparatus and Methods for Nonverbally Communicating Patient Comfort Data," which is incorporated herein by reference in their entirety as if fully set forth herein.

FIELD OF THE DISCLOSURE

This disclosure relates generally to fields of services requiring physical contact between two or more persons such as a patient and a practitioner, and more specifically, to various apparatus and systems and methods for nonverbally communicating patient comfort data.

BACKGROUND

There are a variety of services which require physical contact between two or more persons, such as a patient and a practitioner, in order for the desired service to be adequately administered, and a characteristic of many of such services is a difficulty, on the part of the practitioner, in ascertaining comfort data associated with the patient. Practitioners could in many situations provide a more pleasant (or at least a less unpleasant) service experience and a more effective service result if patient comfort data was readily communicable from patient to practitioner. Unfortunately, under many circumstances such data is not readily communicable due to a variety of factors and resultantly patient experiences are frequently less pleasant than the practitioner could potentially make them while still rendering an effective service.

An exemplary service field which suffers from the limitations described above is the field of massage therapy. Massage therapists manipulate both superficial and deeper layers of muscle and connective tissue using a variety of techniques during which if the pressure applied by the practitioner is too great the patient will potentially experience great discomfort. Not only is patient discomfort intrinsically undesirable, patient discomfort may also lead to a physiological patient reaction known as muscle guarding which inhibits the practitioners ability to deliver the intended therapeutic results. Muscle guarding is a protective response in a muscle, typically wherein the muscle remains in a partially contracted state, which can result from either physical pain or fear of movement. When muscle guarding is occurring it becomes nearly impossible for a massage therapist to achieve the common therapeutic goal of soft tissue lengthening because the effected muscles are actually resisting the accessing and lengthening that the practitioner seeks to induce, e.g. by involuntarily contracting. Accordingly, in the event that the level of pressure applied by the practitioner is too great, e.g. great enough to cause discomfort and induce muscle guarding, the resulting patient experience may be both quite unpleasant and ineffective in achieving the desired therapeutic goals. On the opposite end of the spectrum, too little pressure applied by the practitioner may result in little or no soft tissue lengthening and can also be less pleasurable during the therapy session if a greater amount of depth or pressure was desired. Therefore, the optimum level of pressure for a practitioner to apply during a massage will generally be enough pressure to thoroughly lengthen and knead the patient's soft tissues and muscles but not so much to induce the response of muscle guarding or cause unnecessary discomfort. Moreover, the optimum level of pressure to apply varies widely between patients, even anatomically similar patients, and/or between different parts of a single patient's body, or even within different areas of the same muscle.

Despite the benefits which could be achieved from patient comfort data being readily communicable from the patient to the massage practitioner, such data is infrequently communicated to an appropriate degree. Additionally, often by the time the patient says something, they have already been experiencing discomfort for some time. One reason for this lack of communication is that a patient oftentimes lays face down on a massage table with her head supported by a face cradle which muffles the speech of the patient. Therefore, it may be necessary for the patient to raise her head from the cradle to effectively communicate with the massage practitioner and, due to being in a state of deep relaxation, the patient may simply chose not to put forth the effort of raising her head to communicate. There are many additional factors, which may potentially inhibit communication. The patient may fear that it would be rude to "correct" the practitioner or inform them that they are not doing their job properly, the patient may not understand that there is a great need for communication during the setting of massage therapy and that there is a common misconception of "no pain-no gain," therefore the patient may just grit and bear through any discomfort, and finally, for people who are non-confrontational this interaction may cause some patients to feel socially awkward, the same way someone would feel ill for sending a plate of food back that was not prepared to their liking. Effective massage therapy requires a patient to expose much of their body to an individual whom the patient may not have established a comfortable relationship with. The general social awkwardness perceived by a patient, e.g. due to fully or partially disrobing, or the act of allowing a practitioner whom they have not had the option to build trust with to view and/or touch their body, sometimes hinders the patient's eagerness to communicate regarding their current comfort level or to place any other requests with the practitioner. There exists, therefore, a need for various apparatus and systems and methods for encouraging the communication of patient comfort data from the patient to the massage practitioner in massage therapy settings.

Another exemplary field which suffers from the aforementioned limitations on patient to practitioner communication is the field of dentistry. During a routine teeth cleaning or other oral examination or procedure, the patient frequently experiences a certain level of discomfort resulting from the practitioner's actions. Also, according to some sources an estimated 75% of Americans experience some form of Dentophobia. Although it may not be feasible to eliminate patient discomfort entirely it remains a goal of dental practitioners to limit discomfort as much as possible while still rendering an effective service. For example, it may be necessary to scale underneath the gum line of a patient to remove calculus buildup and it may be impossible to do so without causing any pain whatsoever. However, if the pain should become too extreme or unbearable it is best for the practitioner to be aware of this so that they can take appropriate actions such as administering a localized numbing agent or simply pausing the activity momentarily and then proceeding more delicately. Also, the patient being able to ask for a hard stop in services due to claustrophobia or anxiety, as well as being able to request predetermined parameters such as suction or a rinse during general routine practices, would be beneficial. Due to the nature of dental services, e.g. a patient's mouth is typically open wide and obstructed, it is understandably difficult for a patient to communicate to the practitioner regarding their current level of discomfort. Therefore, there exists an unmet need in dentistry for various apparatus and systems and methods for encouraging the communication of patient comfort data from the patient to the dental practitioner.

Accordingly, this application discloses an apparatus and methods for nonverbally communicating patient comfort data from a patient to a practitioner wherein the practitioner is physically contacting, or otherwise interacting with, the patient as part of the service being rendered. The apparatus and methods may be used by a massage patient to alert a massage practitioner that the level of pressure currently being applied to the patient is either too low and thus ineffectively massaging the patient's soft tissue or is too great and thus is likely to cause or is causing muscle guarding. The apparatus and methods may also be used by a dental patient to alert a dental practitioner that procedure being performed is causing an unsustainable level of discomfort to the patient. In both of these situations, effective communication regarding the patient's level of comfort or discomfort has the potential to increase the effectiveness of the service being rendered and also decreases the likelihood of the patient sustaining an injury due to the service being administered too aggressively. Therefore, the various apparatus and systems and methods for nonverbally communicating patient comfort data solves the long-felt need of empowering a patient to freely and nonverbally communicate information associated with the patient's own level of comfort or discomfort to a practitioner during a service which requires physical contact between the two.

SUMMARY

Systems and methods for nonverbally communicating patient comfort data are disclosed herein. In some embodiments, the systems and methods may include one or more operations including receiving patient comfort data associated with one or more patients through a patient comfort level input device during a course of a treatment session, transmitting the patient comfort data associated with one or more patients received through the patient comfort level input device, and alerting one or more practitioners of the patient comfort data associated with one or more patients received through the patient comfort level input device. In some embodiments, the systems and methods may include at least one of the additional operations of receiving objective data indicating one or more particular treatment types substantially contemporaneously with a performance of the one or more particular treatment types and automatically generating one or more objective treatment session notes for inclusion within at least one of one or more patient charts and one or more medical records. Furthermore, in some embodiments, the systems and methods may include receiving various forms of Subjective Data from patients, including but not limited to patient comfort data, and storing the Subjective Data.

In preferred embodiments, the systems and methods are facilitated through the use of a patient comfort level input device configured to receive patient comfort data, e.g. patient feedback regarding the current level of comfort or discomfort resulting from a service requiring physical contact between a practitioner and a patient, as the patient desires throughout the duration of the service wherein the patient comfort data is contemporaneously transmitted to a practitioner alerting device configured to alert the practitioner through displaying various colors or providing various vibratory indications or audio indications or displaying a graphical representation. In particular, in preferred embodiments the systems and methods may include one or more operations including initiating a performance of a service requiring physical practitioner contact with one or more patients, receiving patient comfort data associated with one or more patients through a patient comfort level input device, and actively modifying the performance of the service requiring physical practitioner contact with one or more patients at least partially in response to at least some patient comfort data received through the patient comfort level input device. Accordingly, it should be appreciated that it is an object of the present disclosure to enable a practitioner to achieve an optimal patient comfort level whilst effectively rendering the service requiring physical contact.

The following embodiments and descriptions are for illustrative purposes only and are not intended to limit the scope of the systems and methods for nonverbally communicating patient comfort data.

BRIEF DESCRIPTION OF THE DRAWINGS

Embodiments of the present disclosure are described in detail below with reference to the following drawings.

DETAILED DESCRIPTION

Systems and methods for nonverbally communicating patient comfort data for a variety of uses such as, for example, within fields of services requiring physical contact between a patient and a practitioner are disclosed herein. Such services include but are not limited to massage therapy, physical therapy, hydrotherapy, spinal or appendage traction, psychiatric sessions, manual & manipulative therapy, electrotherapy, passive and active stretching, occupational therapy, and dentistry. Moreover, the device may be particularly useful when a patient has above-average difficulty speaking or otherwise verbally communicating, e.g. a patient recovering from a stroke which has affected the patient's speech or if a patient is deaf or has speech pathology, or if language is a barrier. It should be appreciated that many specific details of certain implementations are set forth in the following description, and shown in the accompanying figures, to provide a thorough understanding of such implementations. One skilled in the art will understand from the teachings of the present disclosure, however, that the systems and methods for nonverbally communicating patient comfort data may have other possible implementations and that such other implementations may be practiced without one or more of the details described for any particular described implementation, or may have any detail described for one particular implementation practiced with any other detail described for another implementation.

In the following discussion, an exemplary environment 100 for implementing one or more teachings of the present disclosure is described. Next, an exemplary patient comfort level input device 200 for implementing one or more teachings of the present disclosure is described, followed by a description of various embodiments of a practitioner alerting device 300, 400, 500 and a graphical user interface configuration 600 for implementing one or more teachings of the present disclosure. Finally, various possible implementations of the systems and methods for nonverbally communicating patient comfort data are described in relation to block and flow diagrams.

Exemplary Environment

Figure 1:
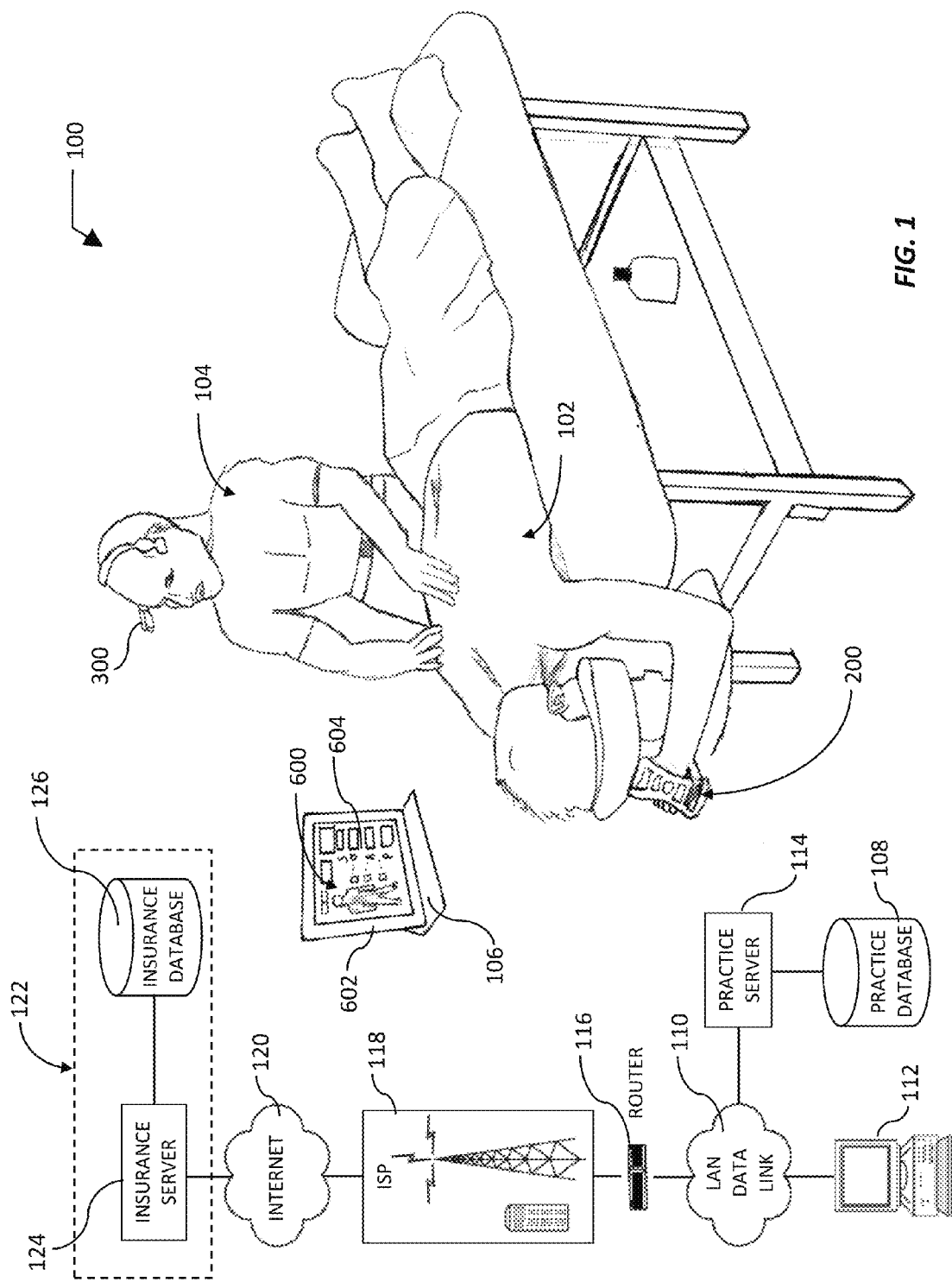
FIG. 1 is a partially schematic illustration of an exemplary environment for implementation of the systems and methods for nonverbally communicating patient comfort data.

FIG. 1 is a partially schematic illustration of an exemplary environment 100 in accordance with an implementation of the present disclosure. It should be understood that the systems and methods disclosed herein may exclude or include numerous elements depicted or not depicted in FIG. 1 and the exemplary environment depicted in FIG. 1 is provided to aid in the understanding of the disclosure but not to limit the disclosure whatsoever. In this implementation, the exemplary environment includes a patient 102 whom is holding a handheld version of a patient comfort level input device 200, and a practitioner 104 whom is wearing a headset-type practitioner alerting device 300. In this implementation, the patient comfort level input device 200 is configured to receive patient comfort level data through patient manipulation of, for example, a joystick coupled to a potentiometer and transmit the patient comfort level data to the practitioner alerting device 300 substantially contemporaneously with patient input. Accordingly, as the practitioner 104 massages various anatomical locations which may have varying degrees of sensitivity due to factors such as muscle spasms and/or lactic acid buildup the patient 102 can with minimal effort nonverbally communicate patient comfort level data to the practitioner with, for example, a simple and nearly effortless thumb movement. Thus, it is an objective of some implementations to encourage communication between the patient 102 and the practitioner 104 such that the practitioner 104 may actively modify the performance of the service, e.g. potentially painful deep tissue massage, in response to the patient's current comfort level. Exemplary environment further includes an implementation of a graphical user interface configuration 600 displayed on a tablet personal computer (PC) 602, preferably including a touchscreen 604 and a waterproof keyboard 106, through which the practitioner 104 may enter objective data related to the patient and/or a particular treatment session to be stored at the tablet PC and/or a practice database 108.

In this implementation, exemplary environment 100 further includes a Local Area Network (LAN) data link 110 that interconnects various clients such as the tablet PC 602, a desktop/laptop PC 112, a practice server 114 for storing and/ or backing up business and other practice related data, and potentially the patient comfort level input device 200 and/or the practitioner alerting device 300. LAN data link 110 interconnects router 116 and one or more of clients 112, 114, 200, 300, and 602. Router 116 provides communication between clients within the LAN data link 110 and also provides communication between one or more of clients 112, 114, 200, 300, and 602 and internet 120 via an Internet Service Provider (ISP) 118. In some implementations, one or more of clients 112, 114, 200, 300, and 602 is configured to communicate via internet 120 with an insurance company 122 having an insurance server 124 and an insurance database 126. Insurance server 124 and insurance database 126 need not be discretely used by insurance company 122 and may be, for example, provided through "cloud computing" or other type of on-demand delivery of IT resources. Potential clients represent generally any computing devices capable of communicating with a routing device and/or otherwise accessing internet 120 such as via any type of telecommunications link (not depicted). The relevancy of the various aforementioned communications abilities will become apparent with reference to the following description and, in particular, FIGS. 7 through 15.

Exemplary Hardware

Figures 2A, 2B, 2C:
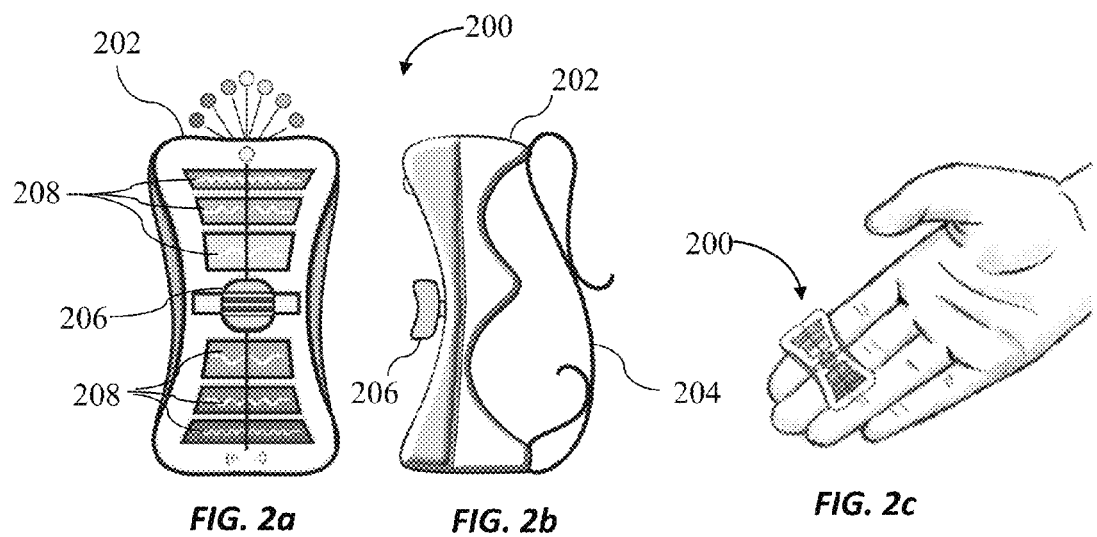
FIGS. 2a and 2b illustrate a front view and a side view of a patient comfort level input device which, in some embodiments, is a component of a system for nonverbally communicating patient comfort data.
FIG. 2c illustrates the patient comfort level input device of FIGS. 2a and 2b being held as intended on the index and middle finger of a patient's hand.

FIGS. 2a and 2b illustrate a front view and a side view of a patient comfort level input device which, in some but not all implementations, is a component of the system for nonverbally communicating patient comfort data. In some embodiments, the patient comfort level input device 200 may include one or more of a handheld housing 202, an adjustable strap 204 for securing the handheld housing to a user's hand, an input receiver 206, one or more display elements 208, and a vibratory intensity indicator (internal to the patient comfort level input device 200 and therefore not depicted). The following embodiments and descriptions are for illustrative purposes only and are not intended to limit the scope of the systems and methods for nonverbally communicating patient comfort data.

It is a purpose of the patient comfort level input device 200 to receive patient feedback as the patient desires throughout the duration of a service requiring physical contact between a practitioner and a patient, especially during service wherein the practitioner may potentially cause the patient discomfort or cause or exacerbate an injury. For example, a massage therapist may provide a patient with the input device 200 prior to performing a massage therapy session. During the massage session the patient may experience discomfort due to the practitioner administering too great of a level of stimulus or pressure to the patient's body and, in response, the patient may indicate through, the input device 200, the level of discomfort being experienced. As used herein, any information regarding the level of comfort or discomfort a patient is experiencing is referred to as patient comfort data. Generally, the patient may input such data into the patient comfort level input device 200 and the apparatus for nonverbally communicating patient comfort data disclosed herein will then alert one or more practitioners of the patient comfort data. Because some embodiments of the patient comfort level input device 200 are designed for being handheld, in certain embodiments, the handheld housing 202 comprises a contoured back configured for added comfort to a user holding the device. Additionally, some embodiments of the patient comfort level input device 200 comprise an adjustable strap 204 for securing the handheld housing to a user's hand. Although the configuration of the patient comfort level input device 200 is a handheld version, other configurations for a patient comfort level input device are contemplated and may be used without departing from the scope of the present disclosure.

In some embodiments, patient comfort level input device 200 comprises a power source, e.g. a rechargeable and/or a removable battery. Preferably, the power source is both rechargeable and a standard battery size such that replacing batteries is not typically necessary yet the apparatus can still be utilized, for example if charging is not an option, by using standard batteries. A prime example of such a situation would be a battery failure just prior to or during the use of the device such that charging would unduly interrupt the service being provided, e.g. a massage therapy session may last for one hour only and stopping the service to charging system components is impracticable during this window of time.

In some embodiments, the input receiver 206 is comprised of a joystick configured and positioned for comfortably receiving input via a patient's thumb. Referring particularly to FIG. 2a, in the illustrated embodiment the type and level of patient input (feedback) corresponds to the direction and distance from center to which the joystick is displaced. For example, some embodiments are configured such that moving the joystick upward (as oriented in FIGS. 2a & 2b) indicates that the patient desires an increased level of stimulus and the amount of increase desired corresponds to the distance from center the joystick is upwardly displaced. Continuing with this example, this embodiment is further configured such that moving the joystick downward (as oriented in FIGS. 2a & 2b) indicates that the patient desires a decreased level of stimulus, the amount of decrease desired similarly corresponding to displacement. The configuration of indicating a desired increase in stimulus by moving the thumb upward and indicating a desired decrease in stimulus by moving the thumb downward will be highly intuitive because of "thumbs up" or "thumbs down" meaning good and bad respectively in popular culture.

In some embodiments, the input receiver 206 comprises a joystick configured to selectively toggle between seven positions each position representing a unique value of patient comfort data. The joystick may be biased to return to a center or neutral position whenever a patient is not actively inputting feedback into the joystick, e.g. by moving it into one of the six non-neutral positions. In this embodiment, three of the positions correspond to a call for varying levels of increased stimulus. For example, the first position above neutral will call for a slight increase in stimulus, the second a moderate increase, and the third a large increase. The remaining three positions, i.e. the three positions below neutral, each correspond to a demand of varying level to decrease stimulus. For example, the first position below neutral will call for a slight decrease in stimulus, the second a moderate decrease, and the third a large decrease (or a call to eliminate stimulus altogether depending on an agreement between the practitioner and patient). Alternatively, the patient comfort level input device 200 does not include discrete positions but rather is configured to receive patient input in a highly sensitive manner such as for example, through a potentiometer coupled to the input receiver 206.

In some embodiments, the input receiver 206 comprises a vibratory intensity indicator configured to vibrate within the input receiver 206 at an intensity corresponding to at least one of the patient desired level of increase in stimulus and the patient desired level of decrease in stimulus. It is an intended purpose of the vibratory intensity indicator to indicate to the patient, through the intensity of vibration felt, as to the current level of desired change in stimulus because in many situations the patient will not visually keep track of what he or she is inputting into the input receiver 206.

In some embodiments, the input receiver comprises one or more display elements 208 to indicate a current input being received from the patient. For example, various display elements 208 may be backlit to illuminate various colors based on a patient comfort data being received.

In some embodiments, the input receiver 206 comprises push button functionality such that a patient can trigger a unique alerting event to the practitioner by depressing the push button. The unique alerting event may be any event capable of alerting the practitioner and, in some embodiments, is intended to represent a patient demand for a response agreed to by the patient and practitioner prior to the unique alerting event being triggered. For example, a practitioner may suggest that a patient depress the input receiver push button if the patient wishes for the practitioner to stop the stimulus altogether, or to call for more focus or detail, or "right there." Such an embodiment would be desirable for patients with acute injuries or other conditions which are highly sensitive to touch. For example, if the patient is an athlete recovering from a torn muscle and is working with a physical therapist in a stretching routine, the patient may experience a quick onset of acute pain and need to immediately stop all external pressure being applied by the physical therapist. The patient will merely need to depress the input receiver 206 and an alarm may sound alerting the practitioner to eliminate externally applied pressure.

As an alternative to a dedicated version of the patient comfort level input device 200, a computer program may be installed onto a general computing device thereby converting the general computing device into a specialized system. For example, a patient may install an application onto a mobile device such as a smartphone and enter patient comfort data through sliding a finger along a touchscreen. Such an implementation may benefit from a patient's existing familiarity with their personnel smartphone thereby reducing inhibition barriers to a patient adopting use of the systems and methods disclosed herein. Moreover, in such an implementation, once installed onto a computing device the application may further enable communication, e.g. via the internet, between the computing device and the practice server 114 and/or practice database 108 in order to provide scheduling services and/or other communication between the patient and the practitioner. For example, in some implementations, the operation of receiving patient comfort data associated with one or more patients through a patient comfort level input device may include enable the patient to enter, through typing or dictation, patient comfort data into the smartphone application whilst currently not in a treatment session or even at the practitioner's practice location. For example, patients are frequently asked about past pain levels at the beginning of a treatment session; however, due to the passage of time it may be difficult for patients to precisely remember the exact level and/or anatomical location of pain which was experienced prior to or in-between treatment sessions. The subjective data collected before the appointment is usually not reassessed until the beginning of the next appointment. In some embodiments, the systems and methods allow for tracking the patient's data through the length of the appointment and until they complete their treatment session. Moreover, the same application may enable easy appointment scheduling and/or request functionality so that a patient does not have to remember to call in, a functionality which may be of particular value when a patient experiences discomfort during non-business hours such as the evening or weekends which would make it likely for the patient to forget to schedule the appointment at a later time. In some embodiments, the systems and methods further enable patients to easily track their progress on their own between treatments sessions, or alert a practitioner of incidence of flaring pain. For example, by gathering data including pain level and type, onset time and duration, activities performed to aggravate symptoms. In some embodiments, the patient may also be able to draw their symptoms on a diagram of a body before a session starts to alert the practitioner of their desires and goals for the treatment session.

Figures 3A, 3B:
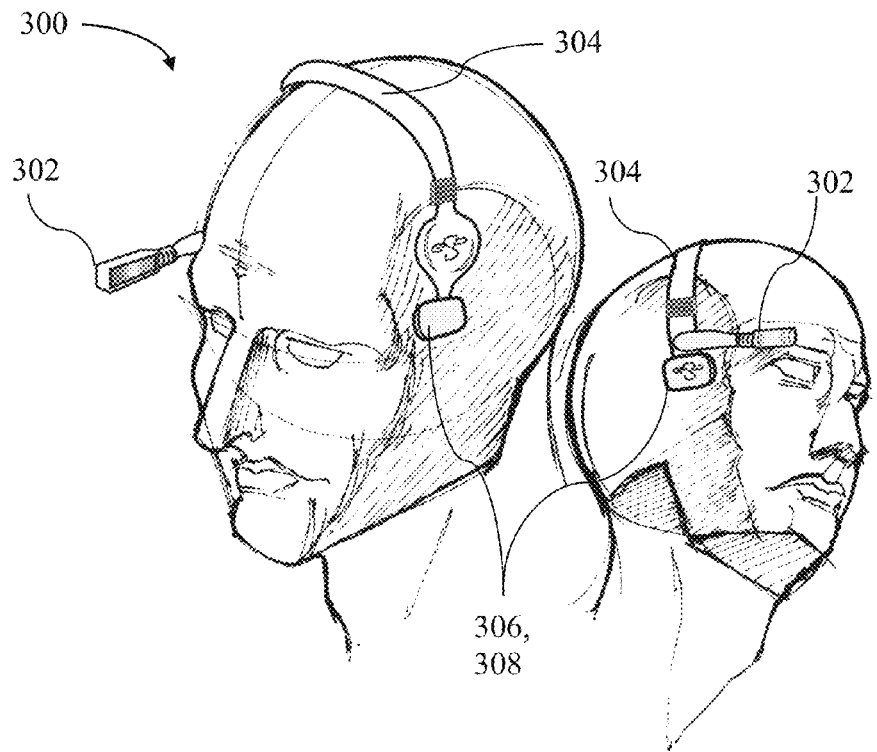
FIGS. 3a and 3b illustrate various views of a headset-type practitioner alerting device which, in some embodiments, is a component of a system for nonverbally communicating patient comfort data.

FIGS. 3a and 3b illustrate various views of a headset-type practitioner alerting device which, in some embodiments, is a component of a system for nonverbally communicating patient comfort data. In one embodiment, the practitioner alerting device 300 may include one or more elements including a peripheral vision patient comfort data indicator 302, an adjustable head band 304, one or more speakers 306, and one or more vibratory intensity indicators 308. In some embodiments, the peripheral vision patient comfort data indicator 302 comprises a display configured for illuminating a spectrum of colors toward the practitioner such that, through her peripheral vision, the practitioner can ascertain the color being displayed without having her vision unreasonably obstructed. In some embodiments, each color the indicator 302 is configured to display corresponds to predetermined patient comfort data. Patient comfort data received via the patient comfort level input device 200 is transmitted to the practitioner alerting device 300 so that the practitioner in continuously alerted as to the patient's current comfort status and can alter the service being provided accordingly. Displaying colors as opposed to integer values to communicated patient comfort data is particularly desirable because practitioners are able to recognize what is being displayed with minimal effort in their peripheral vision whereas an integer or other alphanumeric value would require the practitioner to concentrate on their peripheral vision or focus on the indication.

In some embodiments, the practitioner alerting device is configured to cause one or more speakers 306 to create audible alerts corresponding to patient comfort data received by the patient comfort level input device 200. For example, the speakers 306 may sound a voice alerting the practitioner that the patient has called for stimulus attention at a particular location. Such an occurrence may follow a sequence such as a massage therapist beginning to massage a location of particular interest to the patient at which time the patient may depress a push button feature of the input receiver 206 causing the input device 200 to transmit to the practitioner alerting device 300 patient comfort data indicating that the patient is calling for additional focus on the current particular area thereby causing the speakers to sound the phrase "right there" or "that's the spot."

Moreover, some embodiments are configured to enable the patient to communicate demands as to the direction for the practitioner to move the service to. For example, in some embodiments of the patient comfort level input device 200 a joystick is configured such that it can be depressed slightly downward into a position wherein a full range of 360 degrees of rotation becomes available such that the patient can direct the practitioner to move the service in any direction. For example, the input device may be configured such that when the joystick is not compressed the increase or decrease stimulus commands correspond to a "thumbs up" and "thumbs down" motion but when the joystick is depressed the patient may move the joystick in any direction and the practitioner is alert to move in that direction. The alert may come in the form of a reference to a clock face, e.g. the patient moves the joystick to 45 degrees right of upward center and the speaker commands to move the service to 1:30 or the patient moves the joystick exactly to the right the speaker commands to move the service to 3 o'clock.

In some embodiments, the practitioner alerting device is configured to cause one or more vibratory intensity indicators 308 to output vibratory alerts corresponding to patient comfort data received by the patient comfort level input device 200. For example, the vibratory intensity indicators may vibrate aggressively when the patient is indicating a high level of discomfort but only moderately, lightly or not at all if the patient is indicating only a minor level of discomfort. Moreover, some embodiments comprise two vibratory indicators configured to contact two different parts of the practitioner's body and further configured such that a call by the patient to increase stimulus causes one vibrator to alert the practitioner and a call by the patient to decrease stimulus cause the other vibrator to alert the practitioner. As in other embodiments, the intensity at which the vibrators vibrate may correspond to the level of increase or decrease in stimulus called for by the patient. For example, in an embodiment such as depicted in FIGS. 3a and 3b as 300, elements 308 may each comprise a vibrator and the device 300 may be configured to vibrate against the left and/or right side of the practitioner's head if the patient calls for an increase in stimulus and the right side of the practitioner's head if the patient calls for a decrease.

Figure 4A:
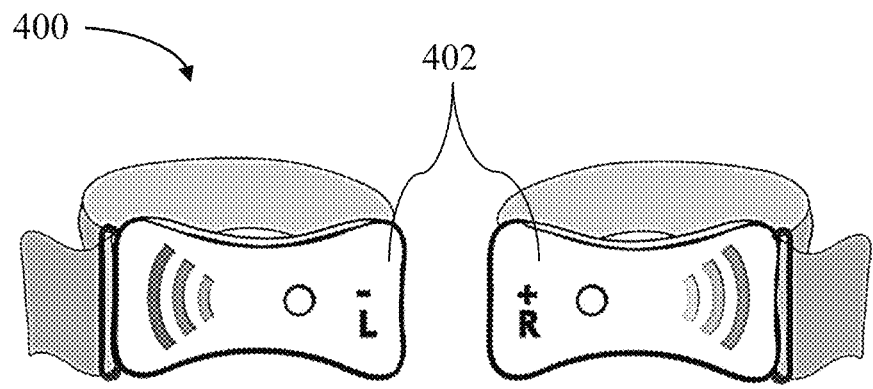
FIGS. 4a and 4b illustrate various views of an arm-worn practitioner alerting device which, in some embodiments, is a component of a system for nonverbally communicating patient comfort data.
Figure 4B:
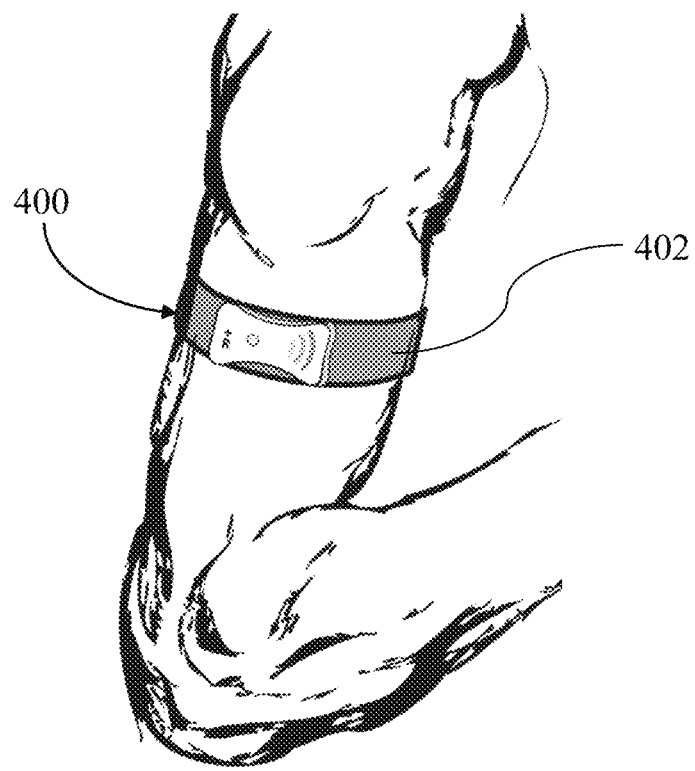
Figure 5:
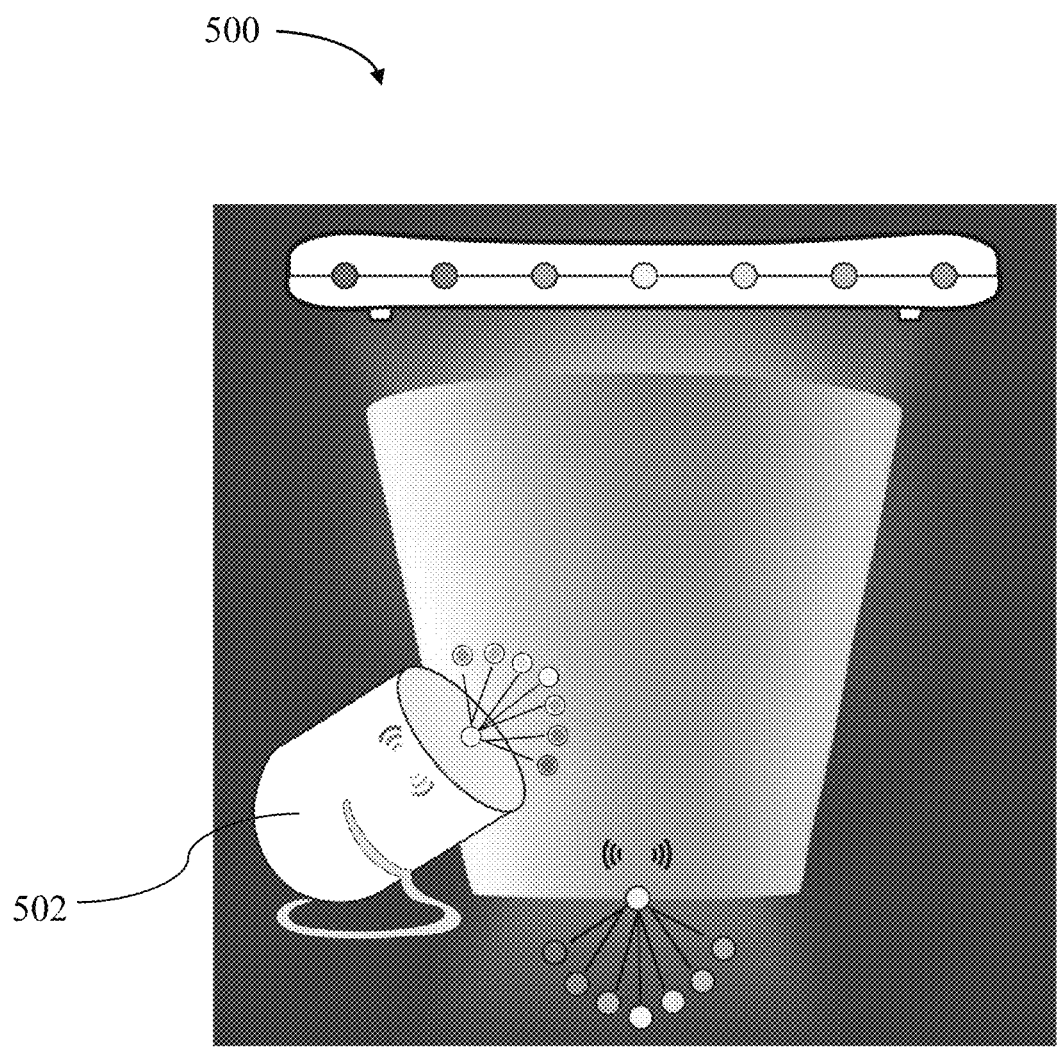
FIG. 5 illustrates an illumination based practitioner alerting device which, in some embodiments, is a component of a system for nonverbally communicating patient comfort data.

FIGS. 4a and 4b illustrate various views of an arm-worn practitioner alerting device which, in some embodiments, is a component of a system for nonverbally communicating patient comfort data. This device is similar to the device 300 in its intended purpose of alerting a practitioner of patient comfort data. In some embodiments, the practitioner alerting device 400 comprises one or more arm worn alerting devices 402. Referring in particular to FIG. 4a, in some embodiments which comprise two arm worn devices, a single arm worn alerting device is intended to be worn on each of a practitioner's two arms and is configured to indicate a desired increase in stimulus by creating a vibration on a single arm and to indicate a desired decrease in stimulus by creating a vibration on the opposite arm. FIG. 5 illustrates an illumination based practitioner alerting device 500 which, in some embodiments, is a component of an apparatus for nonverbally communicating patient comfort data. This device is similar to devices 300 and 400 in that its intended purpose is to alert a practitioner of patient comfort data. In some embodiments, the illumination based practitioner alerting device 500 comprises a light configured to illuminate an area with a variety of colors wherein the precise color which the device emanates corresponds to current patient comfort data. As shown in FIG. 5 the illumination based practitioner alerting device may come in the form of a device including multiple discrete light sources (shown toward top); a can-type light configured to rest on the floor or a table (shown toward bottom left); or a wall sconce type wall mounted lighting fixture (shown at center). Essentially, each variation of the illumination based practitioner alerting device 500 uses various colors to alert the practitioner of patient comfort data. It will be appreciated by one skilled in the art that various other methods of alerting the practitioner may be used.

Although the embodiments described herein are configured to indicate both a desired increase in stimulus and a decrease in stimulus, there are applications wherein a patient will have no reason to call for increased stimulus. For example, in the field of dentistry a common issue remains that a variety of dental services frequently cause pain to the patient such that the patient requests the practitioner to proceed more gingerly. However, dental patients do not typically request for their dentist to more aggressively poke at their gums. Therefore, some embodiments of the system for nonverbally communicating patient comfort data are configured only to receive an indicated level for which to reduce stimulus and/or alert a practitioner of levels of comfort via a pain scale. Such an embodiment may include one or more of a pressure sensor, a load cell, or a torque transducer, wherein one or more of the aforementioned components in configured to receive a user input. An exemplary embodiment is a simple hand held squeeze ball configured to sense the internal pressure created through a patient's hand squeezing down on it. Therefore, a practitioner need only tell a patient to squeeze the ball if the discomfort becomes too great and the practitioner will then be alerted to decrease the stimulus of the pain causing activity. To accommodate for the varying strengths of a patient, some embodiments will incorporate a basic calibration process that can be done by the patient prior to each session.

In some embodiments, the patient comfort level input device 200 is further configured to enable the patient and practitioner to assign different commands to a variety of available patient input values. For example, the input device may have a plurality of push button inputs which, for use in a dental service during which a patient's ability to speak is hindered by the presence of a foreign object within the oral cavity such as practitioner's hands and tools or a dental dam, may be assigned various patient demands such as rinse and suction. Moreover, in such embodiments the positive or negative indications which have been described in the therapeutic massage setting as calling for increased or decreased stimulus can be used in the dental setting to simply indicate "thumbs up" or "thumbs down," for good and not good respectively, when a patient is asked by a practitioner "how are you doing?"

Exemplary Graphical User Interface Configurations

Figure 6A:
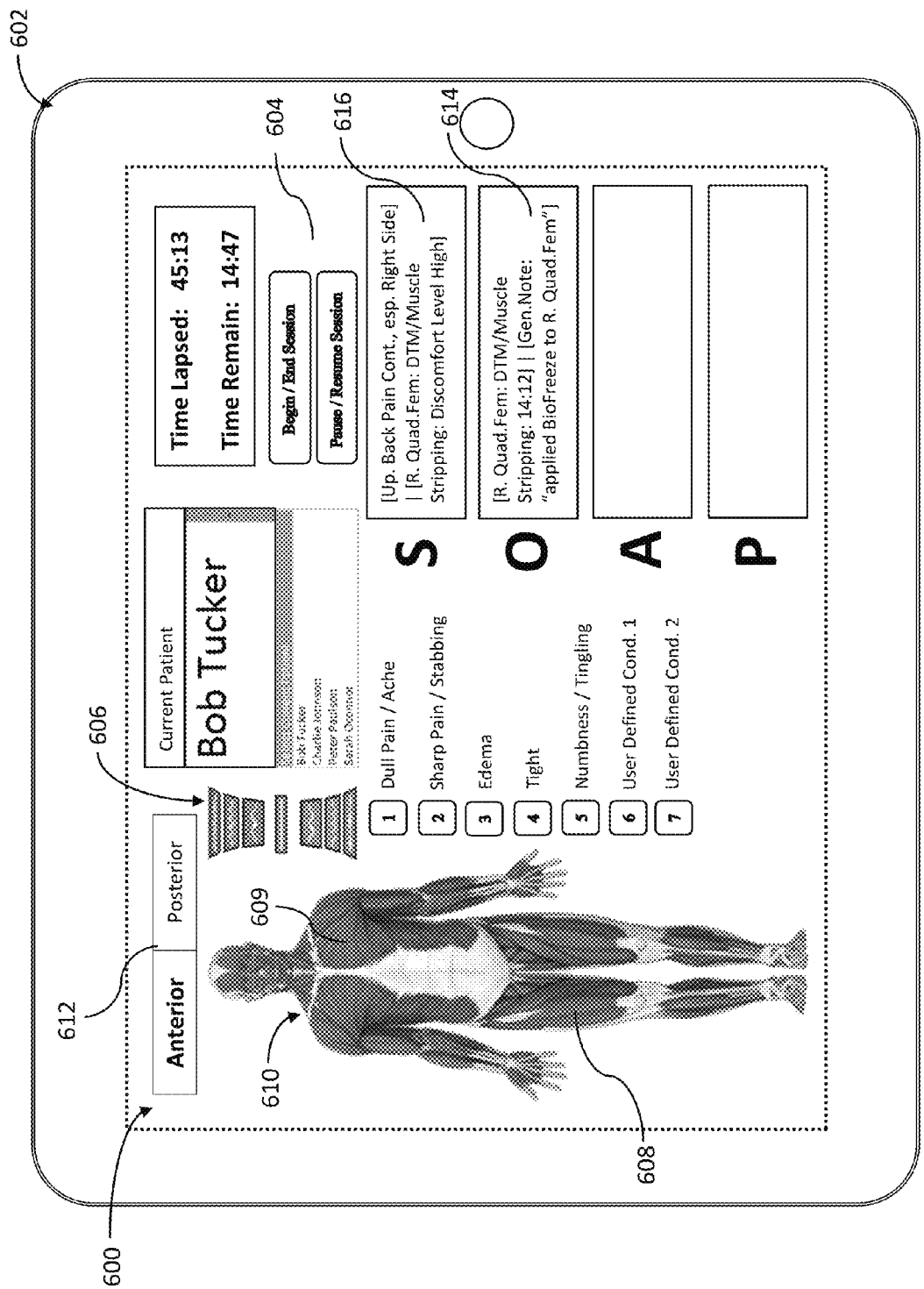
FIGS. 6a and 6b illustrate various graphical user interface configurations which, in some embodiments, are displayed by a system for nonverbally communicating patient comfort data.
Figure 6B:
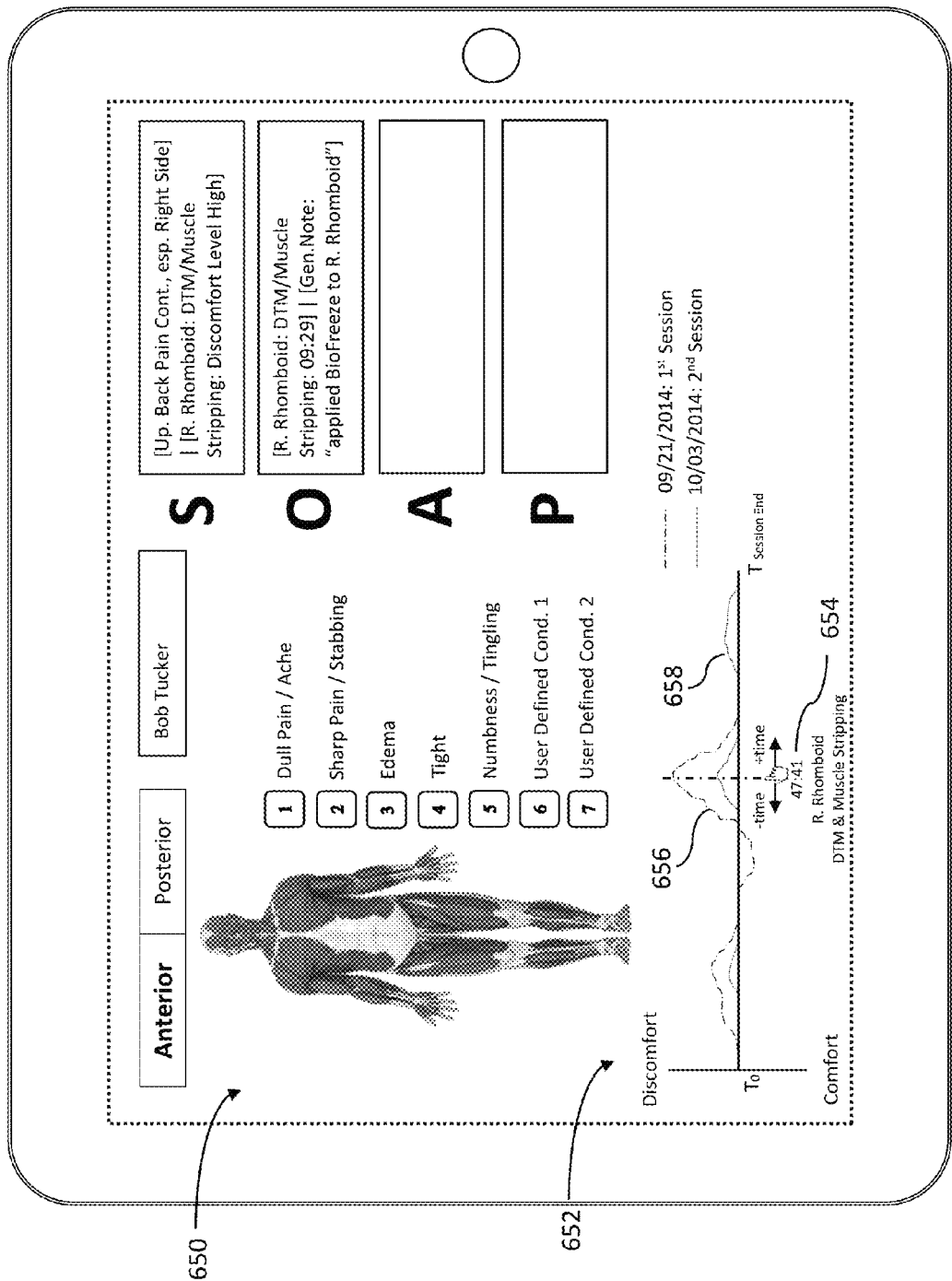

FIGS. 6a and 6b illustrate various graphical user interface (GUI) configurations which, in some embodiments, are displayed by a system for nonverbally communicating patient comfort data. Referring in particular to FIG. 6a, some implementations provide a graphical user interface 600 on the tablet PC 602 which includes the touchscreen 604 through which a practitioner and/or patient may enter data related to one or more treatment sessions, patient charts, and/or medical records. In some implementations, the graphical user interface 600 serves as the practitioner alerting device. For example, the GUI 600 may display a patient comfort level indicator 606 partially resembling the aforementioned patient comfort level input device 200 which graphically displays patient comfort level data as it is received at the patient comfort level input device 200. Thus, in embodiments additional hardware purchasing and management are generally unnecessary to fully implement the system and methods disclosed herein, i.e. many practitioners already possess and/or utilize a tablet PC in their practice and many patients already possess a personal mobile computing device.

In some implementations, the GUI 600 is configured to accept input of objective data related to the treatment session. For example, the GUI 600 may be configured to accept input of objective data indicating one or more particular treatment types performed substantially contemporaneously with the performance of the treatment. As further clarification, in some implementations a practitioner may single-tap on a particular location 608, e.g. a right quadriceps femoris, of an anatomy display 610 to indicate that the practitioner is to begin performing treatment at the particular location. In some implementations, tapping an Anterior/Posterior button 612 causes the anatomy display 610 to toggle between displaying the anterior or posterior of the body. In some implementations, the system then stores subjective data received from the patient, e.g. patient comfort data received through the patient comfort level input device, in relation to the anatomical location at which the practitioner indicated treatment is to be applied. In some implementations, a practitioner may double-tap on a particular location 608 to both indicate that the practitioner is to begin performing treatment at the particular location and also to indicate the type of treatment to be performed, e.g. through a dictation note or a drop-down menu with predefined treatments. Based one objective data and/or subjective data, some implementations of the system are configured to automatically generate notes for inclusion within patient charts and/or medical records. For example, a practitioner may double-tap on the particular location 608 at 22 minutes and 14 seconds into a treatment session and then select from a then appearing drop-down menu the specific treatments of "Deep Tissue Massage" and also "Muscle Stripping." Subsequently, the practitioner may once again double tap on a different particular location 609 (indicating a Left Pectoralis Major Muscle) at 36 minutes and 26 seconds into the same treatment session indicating treatment will begin at the different particular location 609. Utilizing the objective data input during the treatment session, this implementation of the system may automatically generate the note included in the Objective Note Box 614 section of the GUI 600. The note may read, e.g., "[R. Quad.Fem: DTM/Muscle Stripping: 14:12] to indicate that the right quadriceps femoris was treated with "deep tissue massage" and "muscle stripping" for a total of 14 minutes and 12 seconds during the session. In some implementations, the practitioner may also enter manual notes such as that which reads "[Gen.Note: "applied BioFreeze® to R. Quad.Fem"]" indicating that a particular pain relieving substance was applied to the right quadriceps femoris.

Furthermore, in some implementations, the system is configured to store subjective data received from the patient in relation to various objective data received from the practitioner. Moreover, in some implementations the system is configured to automatically generate notes for inclusion within a Subjective Note Box 616 section of the GUI 600 which may also be stored with patient charts and/or medical records. Such a note may read, e.g., "[R. Quad.Fem: DTM/Muscle Stripping: Discomfort Level High]" to indicate that while the practitioner performed Deep Tissue Massage and Muscle Stripping of the right quadriceps femoris the patient experienced a high level of discomfort, as indicated via patient feedback received by the patient comfort level input device. In some implementations, the practitioner and/or may also enter manual notes such as that which reads "[Up. Back Pain Cont., esp. Right Side]" indicating that the patient continues to experience upper back pain, especially on the right side of the body. In some implementations, the GUI 600 is configured to accept input of subjective/objective data related to pain or other symptoms experienced by the patient by tapping one or more symptom indicating boxes (numbered 1-7 on GUI 600) and then drawing directly on the anatomy display 610 to indicate where selected symptoms are occurring.

It should be appreciated that the particular format of the automatically generated notes may differ between implementations. Moreover, one skilled in the art will recognize the Subjective Note Box 616 section and Objective Note Box 614 section of the GUI 600 as incorporating the commonly used SOAP Note method of health care note documentation. In particular, SOAP will be recognized as the acronym for "subjective, objective, assessment, and plan" which is employed by many health care providers, including massage therapists, to write out notes in a patient's chart and/or medical record. In should also be appreciated that various other features may be included within the GUI 600 which assist a practitioner in providing a particular service without departing from the scope of the present disclosure. For example, some implementations may include patient selection drop down menus and/or "Begin/End Session" and/or "Pause/Resume Session" buttons, and or various time lapsed or remaining indications.

Referring in particular to FIG. 6b, some implementations provide a graphical user interface 650 on the tablet PC 602 which includes the touchscreen 604 through which a practitioner and/or patient may enter data related to one or more treatment sessions, patient charts, and/or medical records. Moreover, some implementations of the system for nonverbally communicating patient comfort data are configured to graphically represent at least some of the subjective and/or objective data as a chart 652. As depicted, the chart 652 may include a vertical axis indicating one or more of a level of comfort and a level of discomfort and further include a horizontal axis indicating the range of time from the beginning of a treatment session $T_0$ through the end of a treatment session $T_{Session\ End}$. Information related to particular times of interest within the treatment session may be examined using a cursor (shown as a hand) to drag the particular time of interest 654 forward or backward in time. As depicted in FIG. 6b, the selected time of interest is 47 minutes and 41 seconds into to treatment session (measured from the beginning) and shown directly below the time indicated is an indication of a particular anatomical location which was indicated as being worked on during that time of the treatment session as well as an indication of a particular type of treatment which was indicated as being applied during that time of the treatment session (in accordance with entering objective data as discussed in relation to FIG. 6a). In particular, FIG. 6b depicts that at time of interest 654 of 47:41 (mm:ss) into the treatment session the practitioner was performing Deep Tissue Massage and Muscle Stripping upon the patient's Right Rhomboid.

In addition to objective data as discussed, the chart 652 may further include subjective data 656, 658 such as patient comfort level data entered by the patient through the patient comfort level input device 200 during the course of a treatment session. In some implementations, the chart 652 displays the subjective data from a recent session 658 (indicated as being a $2^{nd}$ session and having occurred on Oct. 3, 2014) along with the subjective data from a previous session 656 (indicated as being a $1^{st}$ session and having occurred on Sep. 21, 2014) thereby graphically illustrating any improvement and/or deterioration in the patient's comfort level during the session as indicated through patient input into the patient comfort level input device 200. Accordingly, both patient and practitioner are able to view a graphical representation of any progress which has been made presumably due to treatment sessions and/or exercises prescribed. Moreover, due to the variety of objective and subjective data the system is capable of collecting it is highly improbable that any two treatment sessions would appear indistinguishable in a digital form. For example, as can be seen and appreciated by subjective data 656 and 658 being displayed in this graphical form the patient comfort data from one session will practically never mirror the patient comfort data from another session. This is particularly the case in implementations have a highly sensitive patient comfort level input device such that even slight variations in patient input are capable of detection and recordation. Accordingly, in some implementations an object of the present system is to create a unique digital representation of at least some of at least one of the received patient comfort data associated with one or more patients and the received objective data related to the treatment session for reasons which will become apparent with reference to FIG. 14. Furthermore, in some implementations, the system further generates one or more reports detailing an amount of time spent on each anatomical location and showing a representation in a static graphical form. Such a report may then be reviewed by other therapists, attending physicians as well as patient payer systems (insurances).

Exemplary Processes for Nonverbally Communicating Patient Comfort Data

Exemplary process for nonverbally communicating patient comfort data will now be described in reference to FIGS. 6-16. For ease of understanding, the flowcharts are organized such that the initial flowchart (FIG. 7) presents an overall "big picture" viewpoint, and thereafter the following flowcharts present possible particular implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and efficient understanding of the various process instances. The following embodiments and descriptions are for illustrative purposes only and are not intended to limit the scope of the systems and methods for nonverbally communicating patient comfort data.

Figure 7:
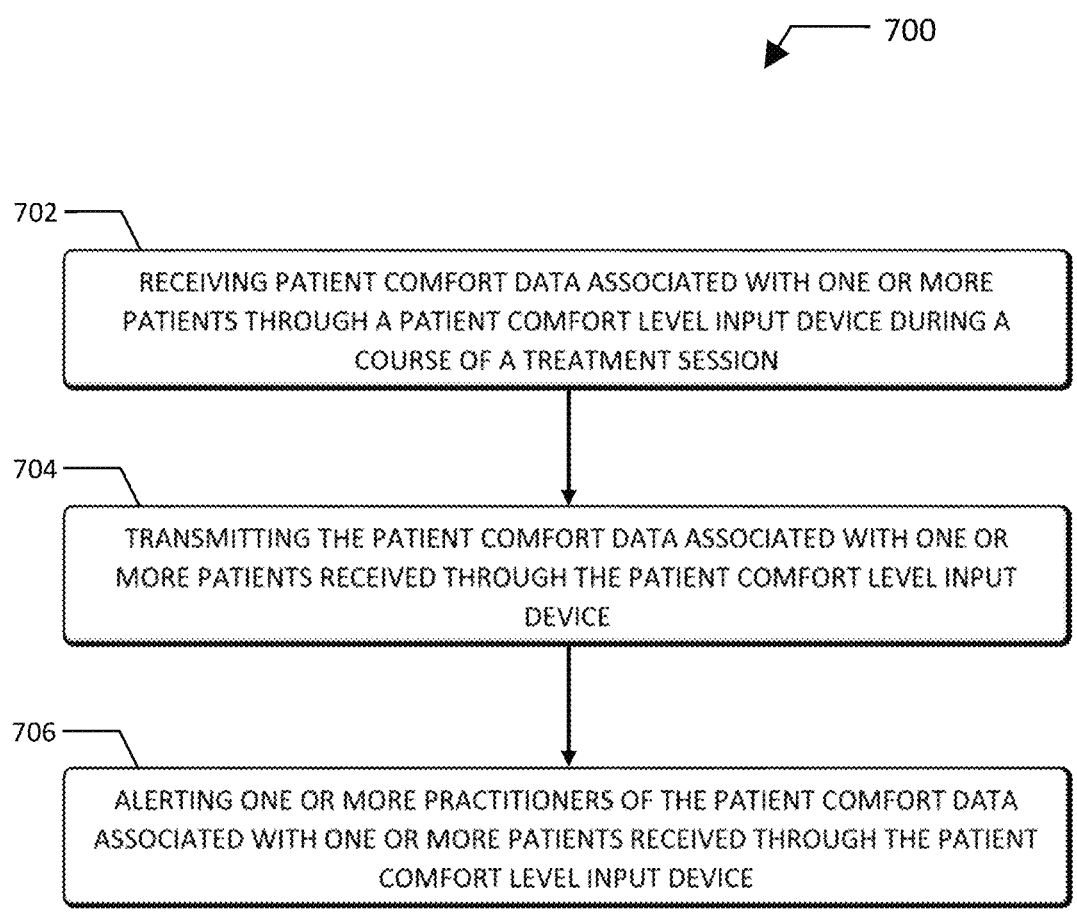
FIGS. 7 through 15 are flowcharts of systems and methods of nonverbally communicating patient comfort data.

FIG. 7 is a flowchart of a method of nonverbally communicating patient comfort data 700 in accordance with another implementation of this disclosure. In this implementation, the method 700 includes receiving patient comfort data associated with one or more patients through a patient comfort level input device during a course of a treatment session at 702. For example, some implementations may include receiving feedback from a patient during the course of a massage therapy session while the patients head is face down in a head cradle through either a dedicated patient comfort level input device as described in relation to FIG. 2 or through a personal computing device (e.g. a patient's cell phone) which has been specifically configured (e.g. by installation of an application or "app") to receive patient feedback. Preferably, patient comfort level input devices require very little effort and thought on the part of the patient and, accordingly, must be configured specifically for a variety of fields of use such as; for example, massage therapy, dentistry, physical therapy, and many other services industries requiring physical contact between two individuals. In fields where the patient is unlikely to provide data indicating that a particular stimuli is comfortable it may only be necessary to communicate discomfort; accordingly, implementations for such fields may be very simple to operate and require little or no orientation of the device, e.g. a squeeze ball implementation simply measuring pressure exerted by a patient squeezing due to discomfort. The method 700 may further include transmitting the patient comfort data associated with one or more patients received through the patient comfort level input device at 704. In some implementations, transmitting the patient comfort data at block 704 is configured to execute automatically such that no set up is required. For example, in certain implementations wherein the system for nonverbally communicating patient comfort data is comprised of a single unit, e.g. implementations wherein the practitioner alerting device and the patient comfort level input device are comprised within a single unit, the patient comfort data is transmitted internally and need not establish a wireless connection whatsoever. An example of such an implementations is a hand held squeeze ball that sounds a simple alarm in the event a predetermined internal pressure is reached due to a patient's gripping forces on the squeeze ball (e.g. a possibly natural response to a dental practitioner cleaning calculus around the gum line or drilling a cavity). The method 700 may further include alerting one or more practitioners of the patient comfort data associated with one or more patients received through the patient comfort level input device at 706. For example, one or more of practitioner alerting devices 200, 300, 400, and 500 and/or GUI 600 displaying patient comfort level indicator 606 may be placed within a perceptible sensory range (e.g. within a range within which the practitioner may hear an audible alert or see a visual alert or feel a vibratory alert). The practitioner, therefore, may modify or terminate physical contact based on the patient feedback received.

Figure 8:
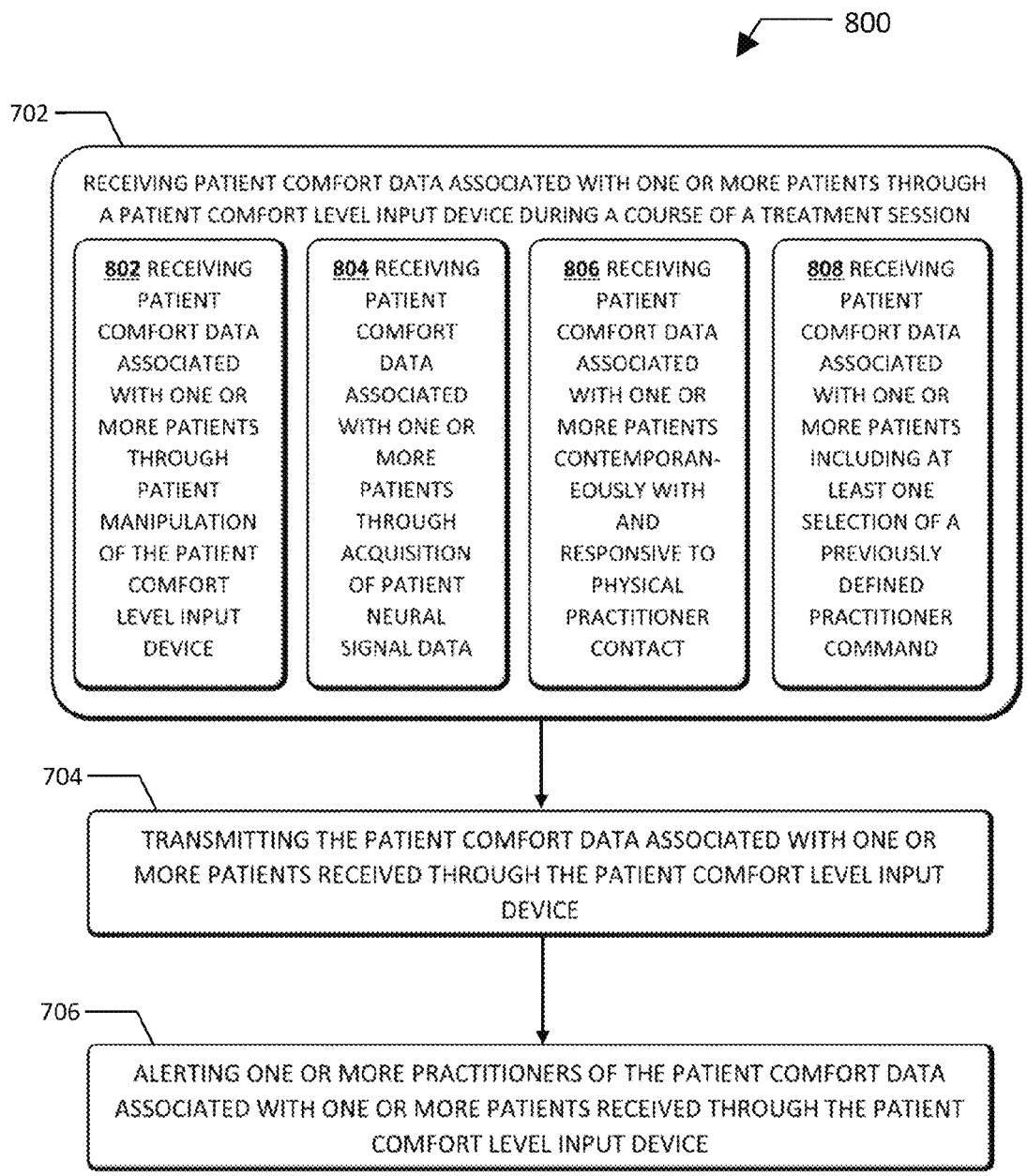

With reference to FIG. 8, in at least some implementations, receiving patient comfort data associated with one or more patients through a patient comfort level input device during a course of a treatment session at 702 may include receiving patient comfort data associated with one or more patients through patient manipulation of the patient comfort level input device at 802. For example, as described in reference to the exemplary environment of FIG. 1 and the patient comfort level input device of FIG. 2 one or more patients may manually manipulate (e.g. hold the device in their hand and use a thumb to control an input) a device configured to receive patient input (e.g. device 200 or a smartphone with an application installed transforming the smartphone into a patient comfort level input device). The patient manipulation need not be finely manipulating a device and may be simply squeezing a device. In further implementations, receiving patient comfort data associated with one or more patients through a patient comfort level input device during a course of a treatment session at 702 may include receiving patient comfort data associated with one or more patients through acquisition of patient neural signal data at 804. For example, the one or more patients may simply wear an electroencephalography (EEG) based patient comfort level input device such as an EEG headset configured with wireless technology such as Bluetooth® standard for exchanging data over short distances between electronic devices. Exemplary of such is set forth in U.S. patent publication no 2014/0276188 a1, herein incorporated by reference. In some implementations, an EEG based patient comfort level device is configured to communicate with a patient manipulated patient comfort level input device such as device 200 in order to quickly "train" the EEG unit as to a particular patient's unique neural parameters. For example, the patient enters patient comfort data into the patient manipulated device (e.g. 200) while the EEG based patient comfort level input device simultaneously tracks and records the neural parameters associated with the manually entered patient comfort data. In such implementations, once the EEG based patient comfort device is "trained" the patient no longer needs to manually enter any feedback. In further implementations, receiving patient comfort data associated with one or more patients through a patient comfort level input device during a course of a treatment session at 702 may include receiving patient comfort data associated with one or more patients contemporaneously with and responsive to physical practitioner contact at 806. For instance, the patient may have a highly fluctuating level of pain due to the practitioner performing a service upon the patient which almost certainly will cause discomfort at some point during the service despite causing discomfort being undesirable and unnecessary to effectuate the treatment. As an example, a dental practitioner will almost certainly cause pain at some point during a routine teeth cleaning, especially if a high level of calculus has built up around the gum line; however, causing pain is both undesirable and unnecessary to effectuate treatment. As another example, a massage therapist performing a deep tissue massage may be aiming to increase circulation, provide therapeutic manipulation to scar tissue and adhesions, and/or blockages and this process may almost certainly cause moderate to severe discomfort to the patient if the treatment is to have any effect; moreover, with massage therapy in particular there can be a fine line between that stimulus which causes comfort and that slightly increased stimulus which causes discomfort. Accordingly, in each of these examples it may be desirable to monitor the patient's comfort/discomfort contemporaneously with and responsive to the physical contact thereby allowing the practitioner to modify the treatment responsively. In further implementations, receiving patient comfort data associated with one or more patients through a patient comfort level input device during a course of a treatment session at 702 may include receiving patient comfort data associated with one or more patients including at least one selection of a previously defined practitioner command at 808. For example, in a dental implementation the patient comfort level input device may include one or more buttons including previously defined commands including but not limited to: rinse (instructing the dental practitioner to rinse the patient's mouth); suction (instructing the dental practitioner to provide suction within the patient's mouth); and brief pause (instructing the dental practitioner to simply pause the current activity for a brief moment before resuming, e.g. so that patient can relax her mouth). For another example, in a massage therapy implementation the patient comfort level input device may include one or more buttons including previously defined commands including but not limited to: one or more anatomical locations (e.g. a button to direct a massage therapist to massage the lower back); return to previous location (e.g. a button to direct the massage therapist to re-direct attention to a previous anatomical location such as if the therapist moves from the lower back to the shoulder and the patient wishes for him to continue to work on the lower back rather than moving onto the shoulder).

Figure 9:
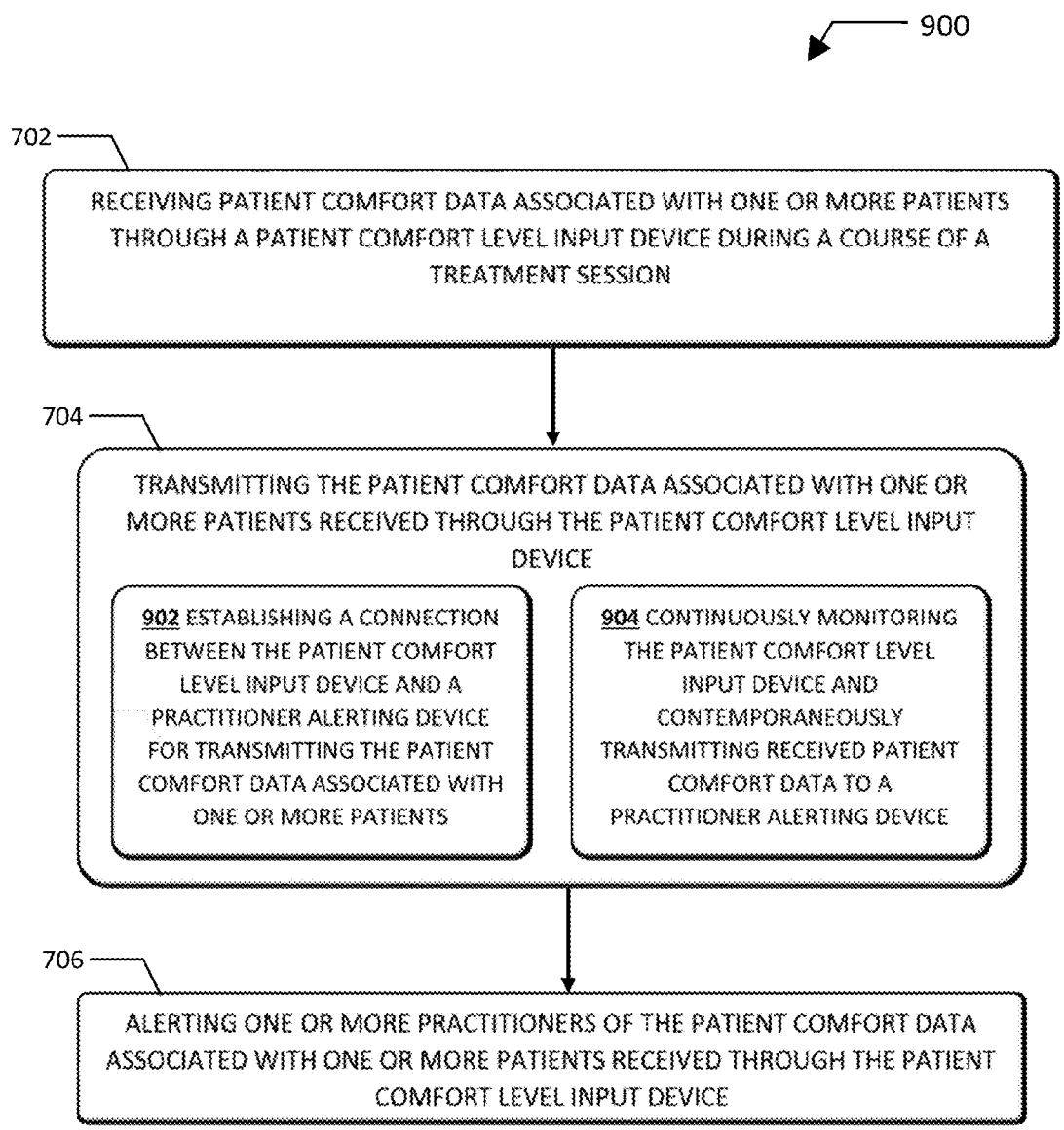

With reference to FIG. 9, in at least some implementations, transmitting the patient comfort data associated with one or more patients received through the patient comfort level input device at 704 may include establishing a connection between the patient comfort level input device and a practitioner alerting device for transmitting the patient comfort data associated with one or more patients at 902. For example, the patient comfort level input device may transmit data through a wired or wireless connection. Any suitable method of establishing a connection, whether currently known or subsequently developed, may be used to accomplish this operation such as, for example, Bluetooth™ technology, or Wi-Fi™ technology, or ZigBee™ technology may be used in various implementations. In at least some implementations, transmitting the patient comfort data associated with one or more patients received through the patient comfort level input device at 704 may include continuously monitoring the patient comfort level input device and contemporaneously transmitting received patient comfort data to a practitioner alerting device at 904. For example, any patient comfort data received may be transmitted substantially contemporaneously, e.g. transmitted with minimal delay due to basic electronic processing times which may be imperceptible to humans, to the practitioner alerting device thereby immediately informing the practitioner of the patient's current comfort level. The operation at 904 is beneficial because in some implementations an intended purpose of the system and method disclosed herein is to facilitate real time, i.e. instantaneous, feedback regarding a service as it is being provided such that a practitioner can immediately respond to the feedback and improve the patient's comfort. The benefits of this operation will be immediately apparent to practitioners in certain fields of service because many such practitioners receive only limited feedback after a service has been provided or no feedback at all. For example, the field of massage therapy there currently exists a fairly high churn ratio of patients, i.e. patient retention is an ongoing struggle for massage therapists. A large factor in this undesired churn is that a patient does not feel completely satisfied with the massage service rendered; however, oftentimes the practitioner is provided with no feedback whatsoever from the patient and otherwise has no way to know a patient is dissatisfied. The methods and systems disclosed herein facilitate open communication and feedback to enable the patient to effortlessly instruct the practitioner throughout the entire duration of the service being rendered and thereby mitigate, at least partially, the aforementioned issue of churn. Embodiments wherein the patient comfort data is communicated by way of vibrations felt by the practitioner are also intended to benefit the many massage therapists who prefer to "look with their hands" and therefore keep their eyes closed to heighten their ability to physically sense with their hands how a patient's body is responding to the therapy.

Figure 10:
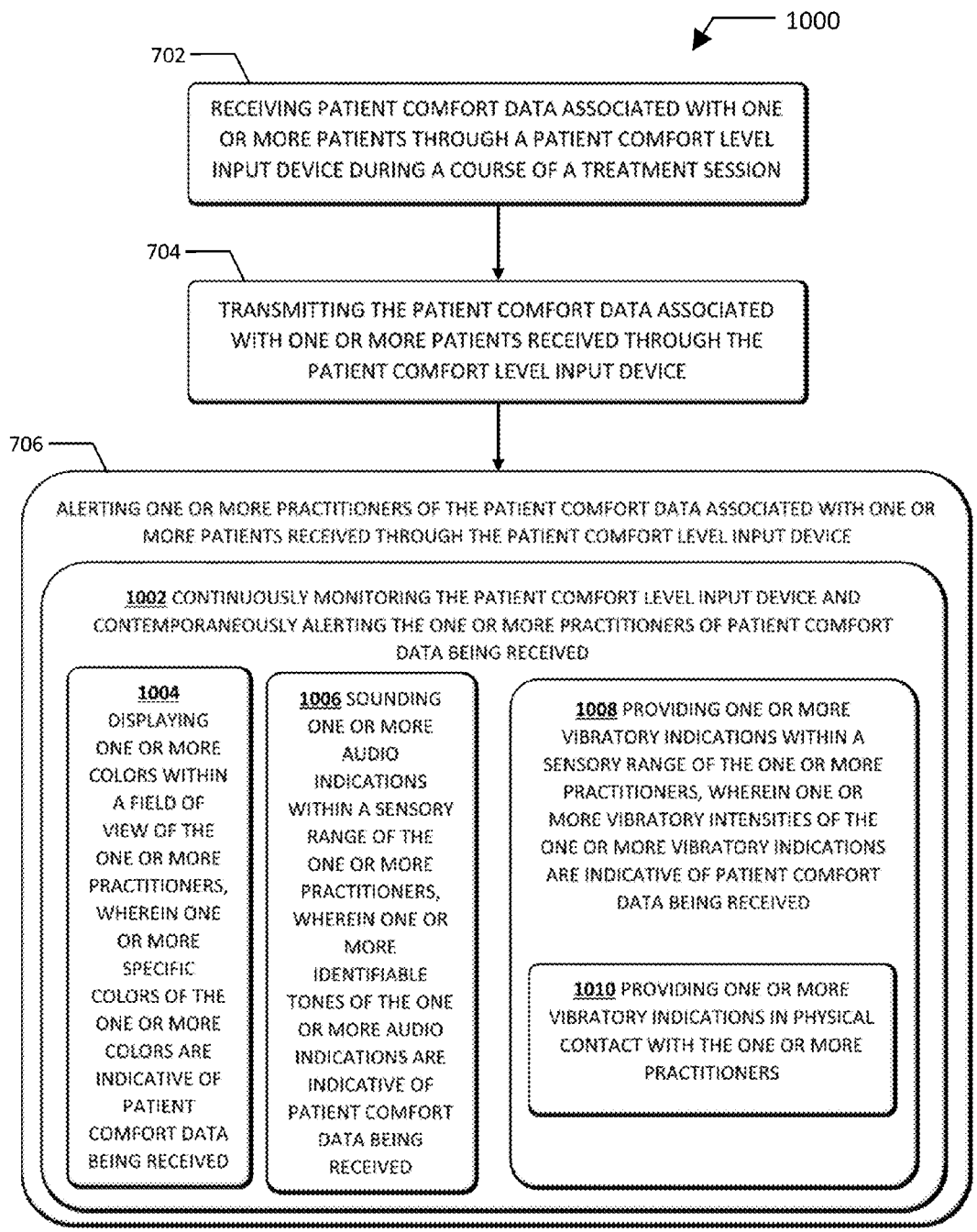

With reference to FIG. 10, in at least some implementations, alerting one or more practitioners of the patient comfort data associated with one or more patients received through the patient comfort level input device at 706 may include continuously monitoring the patient comfort level input device and contemporaneously alerting the one or more practitioners of patient comfort data being received at 1002 (e.g. alerting the practitioner of patient feedback in substantially real-time during the course of the treatment session thereby enabling the practitioner to improve the service being performed). Furthermore, in some implementations, the operation at 1002 may include displaying one or more colors within a field of view of the one or more practitioners, wherein one or more specific colors of the one or more colors are indicative of patient comfort data being received at 1004 (e.g. displaying colors indicative of patient feedback as it is received within the peripheral vision of a practitioner using peripheral vision patient comfort data indicator 302; or e.g. illuminating and area within the visual range of the practitioner with colors indicative of patient feedback using illumination based practitioner alerting device 500). Furthermore, in some implementations, the operation at 1002 may include sounding one or more audio indications within a sensory range of the one or more practitioners, wherein one or more identifiable tones of the one or more audio indications are indicative of patient comfort data being received at 1006. For example, the system may be silent when no discomfort is indicated but then initiate a sounding of a low-frequency "ping" sound (e.g. a ping at 0.5 Hz or 1 ping per every 2 second) upon receipt of an indication of low-level patient discomfort, followed by a mid-frequency "ping" sound (e.g. 1 Hz) upon an indication of mid-level patient discomfort, and finally a high-frequency "ping" (e.g. 2-3 Hz) upon an indication of high-level patient discomfort. An alternative sound (i.e. not the same "ping" used to indicate discomfort) may be used to indicate comfort such as when a massage therapist's current actions feel good to the patient. Furthermore, in some implementations, the operation at 1002 may include providing one or more vibratory indications within a sensory range of the one or more practitioners, wherein one or more vibratory intensities of the one or more vibratory indications are indicative of patient comfort data being received at 1008. For example, similar to the implementation described at 1006, an increasing vibratory frequency may be used to indicate an increasing level of discomfort. In some implementations, a steady frequency may be used to indicate discomfort while a vibratory indication oscillating between one or more frequencies may indicate comfort. Moreover, in some implementations comfort is indicated by a first device vibrating and discomfort is indicated by a second device vibrating (e.g. a two arm version of the arm-worn practitioner alerting device 400 wherein vibration on left arm indicates discomfort and vibration on right arm indicates comfort or a headset version with vibrators mounted on each side of the practitioner's head). Furthermore, in some implementations, the operation at 1008 may include providing one or more vibratory indications in physical contact with the one or more practitioners at 1010 (e.g. arm-worn practitioner alerting device 400).

Figure 11:
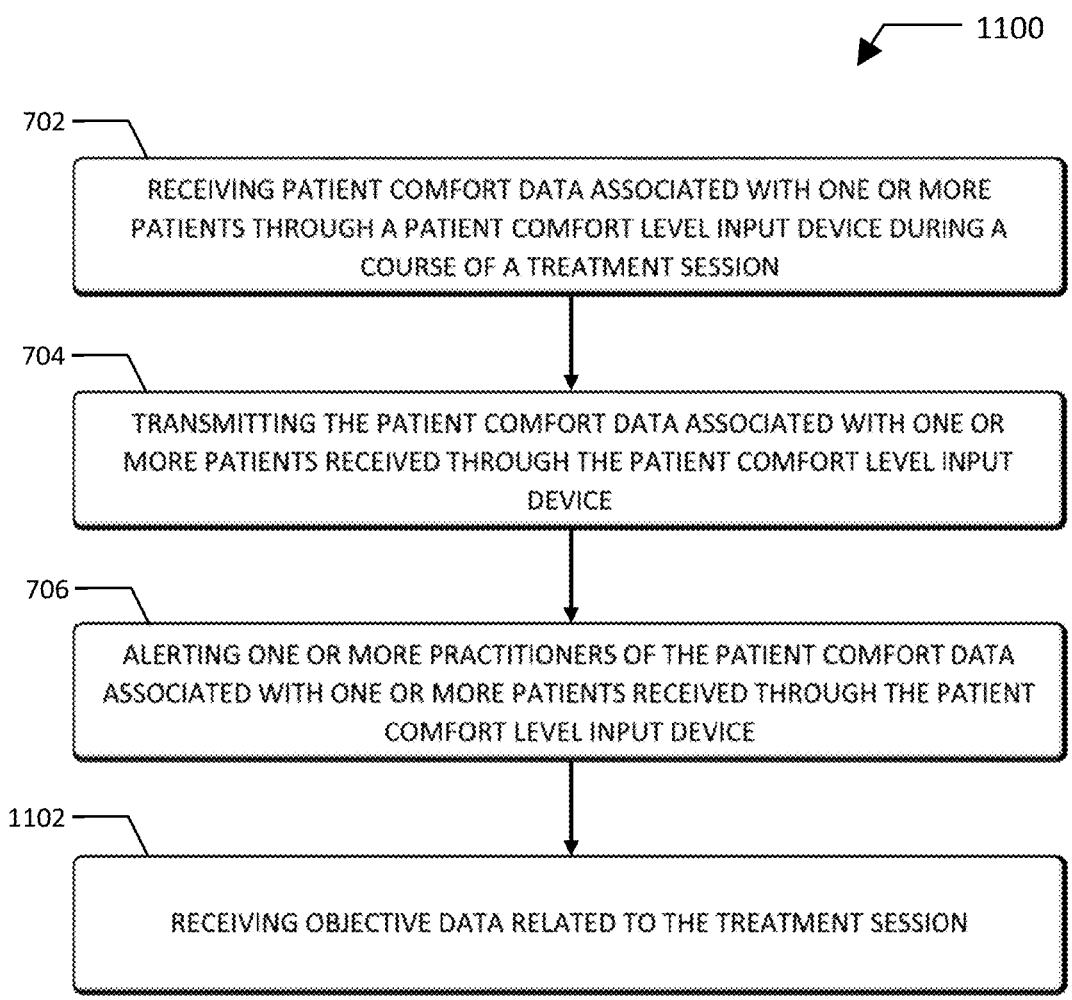
Figure 12:
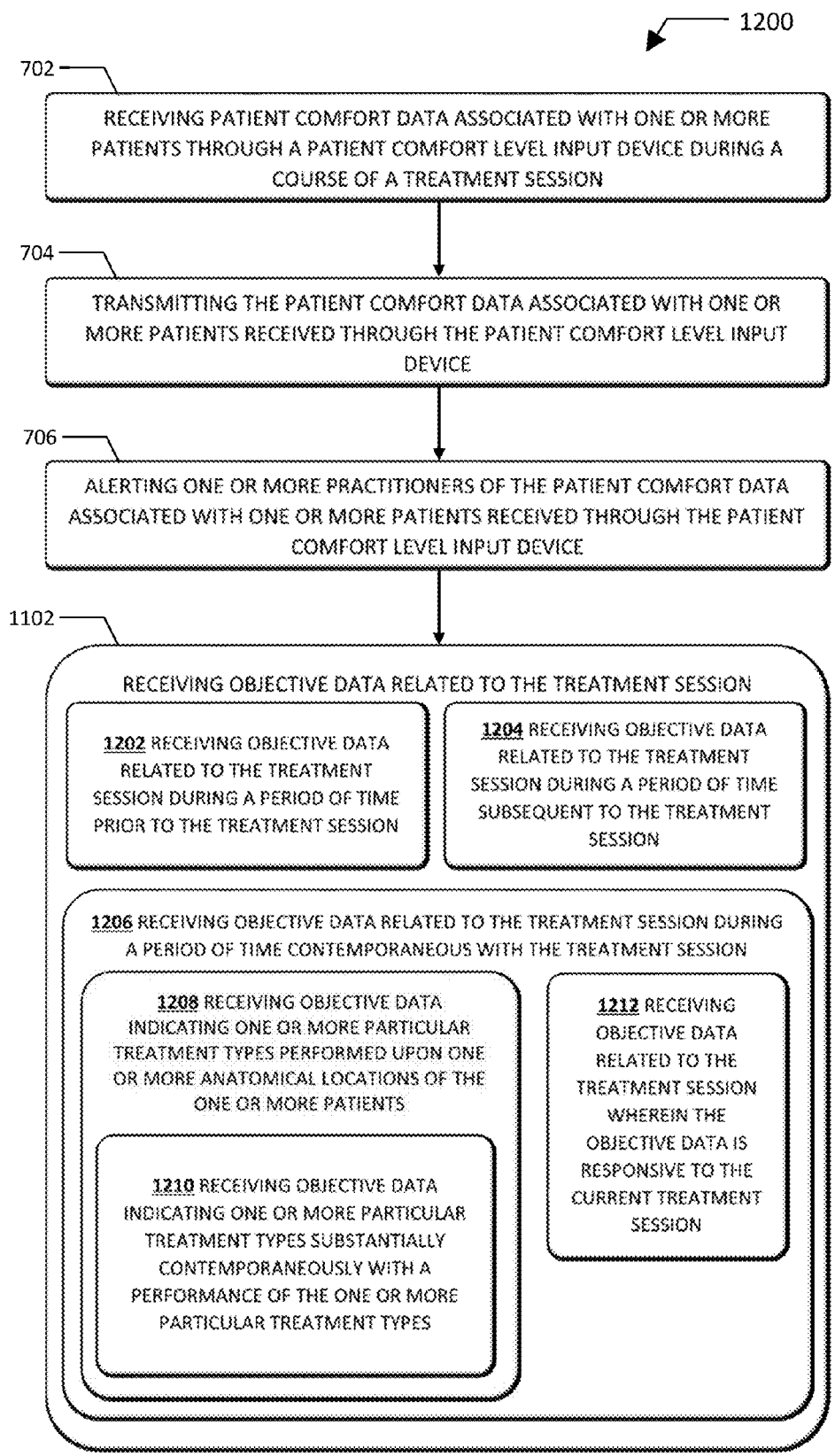
Figure 13:
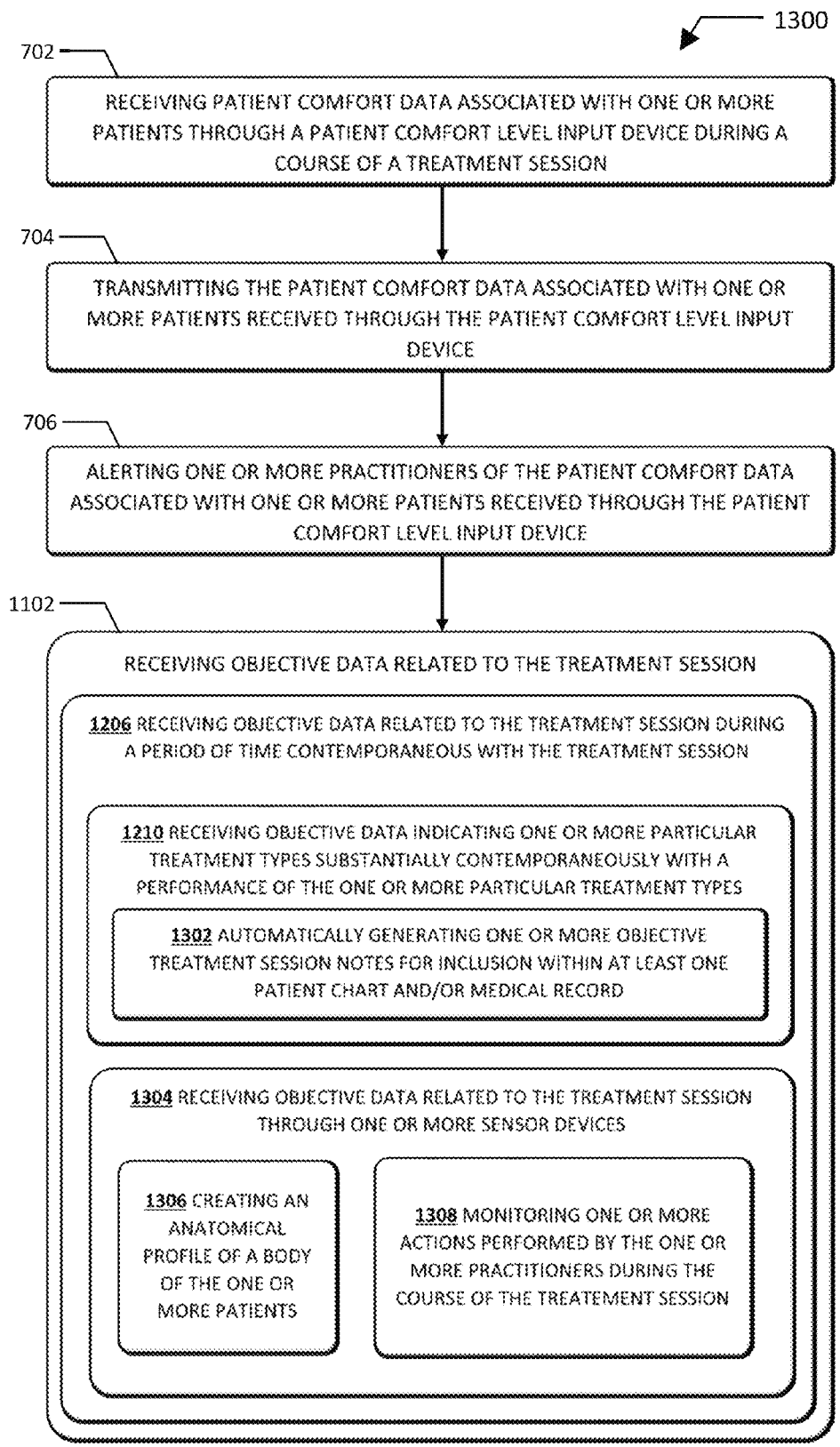

With reference to FIG. 11, in at least some implementations, in addition to operations at 702, 704, and 706 as described supra, the method may further include receiving objective data related to the treatment session at 1102. For example, in accordance with some implementations the method may include receiving data regarding patient name, health history information, health insurer and/or policy data, information regarding vital signs (e.g. temperature, pulse, blood pressure, respiration), results of physical tests performed, sensory test results, edema, laboratory, radiology or other testing performed on a patient, data regarding drugs prescribed and/or taken (including non-prescribed drugs), or any other objective data desirable to receive in relation to treatment of a patient. With reference to FIG. 12, in at least some implementations, receiving objective data related to the treatment session at 1102 may include receiving objective data related to the treatment session during a period of time prior to the treatment session at 1202. For example, for various reasons many practitioners require patient's to fill out a new patient intake form prior to a first treatment session and such intake forms routinely request objective types of data (e.g. "Have you had orthopedic surgery in the past?" or "Did your current symptoms arise gradually?" or "How long have you been experiencing your chief complaint?"). As used herein, the term "objective data" includes but is not limited to and all objective type information appropriately entered into SOAP medical charting, and more particularly entered into the Objective portion of the SOAP chart including but not limited to tests and measurements done on client (e.g. vital signs, range of motion (ROM) measurements, PT special tests, and manual muscle tests and/or details of the interventions (e.g. frequency and duration treatment and equipment used). Furthermore, in some implementations, the operation at 1102 may include receiving objective data related to the treatment session during a period of time subsequent to the treatment session at 1204. For example, in an effort to the effectiveness of a prescribed treatment regimen a Physical Therapist may inquire as to whether the patient has been routinely completing (e.g. on a day-to-day basis) prescribed exercises such as home traction exercises aimed at relieving the buildup of spinal pressures. Another example consistent with operation 1204 may be manually objective data entry documenting treatment performed during a treatment session (e.g. "12 minutes of Deep Tissue Massage on Right Rhomboid resulting in noticeable muscle release). Furthermore, in some implementations, the operation at 1102 may include receiving objective data related to the treatment session during a period of time contemporaneous with the treatment session at 1206. For example, a massage practitioner may utilize the GUI 600 on the tablet PC 602 to enter objective data such as a particular treatment type to be performed or a particular prescribed medicine or exercise regimen during a treatment session, to analyze subjective input (e.g. patient comfort data) corresponding to anatomical positions that received the treatment. Furthermore, in some implementations, the operation at 1206 may include receiving objective data indicating one or more particular treatment types performed upon one or more anatomical locations of the one or more patients at 1208. For example, during the course of performing a massage on a patient a massage practitioner may use the touchscreen 604 to double-tap on the particular location 608 and then through a drop-down menu or a dictation function which translates voice recordings to written text indicate that deep tissue massage and/or electrotherapy was or will be performed at location 608, and for what duration. Furthermore, in some implementations, the operation at 1208 may include receiving objective data indicating one or more particular treatment types substantially contemporaneously with a performance of the one or more particular treatment types at 1210. For example, a massage practitioner may enter objective data into the system in accordance with operation 1208 immediately prior to (e.g. substantially contemporaneously with in that insignificant time passes between entering the data and initiating treatment) initiating the performance massaging the particular anatomical location 608. Furthermore, in some implementations, the operation at 1206 may include receiving objective data related to the treatment session wherein the objective data is responsive to the current treatment session at 1212. For example, receiving objective data from a chiropractor indicating that a particular spinal manipulation was being performed when a patient indicated a high level of discomfort. Referring now to FIG. 13, in at least some implementations, receiving objective data indicating one or more particular treatment types substantially contemporaneously with a performance of the one or more particular treatment types at 1210 may include automatically generating one or more objective treatment session notes for inclusion within at least one patient chart and/or medical record at 1302. For example, in accordance with the implementation of GUI configuration 600 described supra, based upon the receipt of data indicating a first time that the performance of a first particular treatment is initiated followed by a subsequent indication of a second time that the performance of a second particular treatment is initiation, the times may be subtracted to arrive at a total amount of time which the first treatment was performed. Moreover, the an indication of precisely what the first treatment is may also be entered during the course of performance of the treatment session and used in the generation of a treatment session note. As a specific example, a note reading "[R. Quad.Fem: DTM/Muscle Stripping: 14:12]" to indicate that the right quadriceps femoris was treated with "deep tissue massage" and "muscle stripping" for a total of 14 minutes and 12 seconds during the session may be generated as described supra in reference to GUI 600. It should be appreciated that the detailed description of the GUI configurations 600 and 650 are highly relevant in attaining an understanding of at least operations 1102, 1206, 1208, 1210, and 1302.

Still referring to FIG. 13, in at least some implementations, receiving objective data related to the treatment session during a period of time contemporaneous with the treatment session at 1206 may include receiving objective data related to the treatment session through one or more sensor devices at 1304. For example and in reference to exemplary environment 100, a thermographic camera (also referred to as an infrared camera or thermal imaging camera) may be affixed above the patient 102 and configured to take a thermal image of the patient. As another example, one or more electromyogram (EMG) sensors may be used to record electrical activity within various muscle groups experiencing muscle spasms at various times during the treatment session to determine if the level/intensity of spasm has decreased during the treatment session. Furthermore, in some embodiments, objective data related to the treatment session may be obtained through EMG sensors worn by the practitioner (e.g. EMG sensors embedded into armbands) wherein the EMG sensors detect and translate muscle activity of the practitioner into one or more identifiable massage strokes and/or massage intensity levels. In some implementations, receiving objective data related to the treatment session through one or more sensor devices at 1304 may further include creating an anatomical profile of a body of the one or more patients at 1306. For example, in accordance with the previous example of using a thermal imaging camera to take a thermal image of a patient's body, the "raw" thermal image may then be converted to an patient specific anatomical profile of the patient's body (e.g. a bare outline profile or border of the patient's body) and may further be converted into a standard anatomical profile (i.e. not patient specific) for ultimate reproduction on patient charts. This feature may be important to the many persons whom are self-conscious with regard to their bodies and, therefore, would be uncomfortable having their patient specific (actual) profile being reproduced on medical charts viewable by office personal other than the patient's specific practitioner. In some implementations, receiving objective data related to the treatment session through one or more sensor devices at 1304 may further include monitoring one or more actions performed by the one or more practitioners during the course of the treatment session at 1308. For example, a thermographic camera, or RFID sensors may be used to monitor the finger, hand and elbow placement of a massage therapist throughout the duration of a massage therapy session in order to document at least some information (e.g. at least anatomical location data) related to treatments actually performed, and to compare and interpret subjective data (e.g. patient comfort data) from the patient device 200 that was captured to that location. Such data may subsequently be valuable for comparison against one or more prescribed treatments by an insurer to confirm that payments are being applied toward only treatments covered by a patent's policy.

Figure 14:
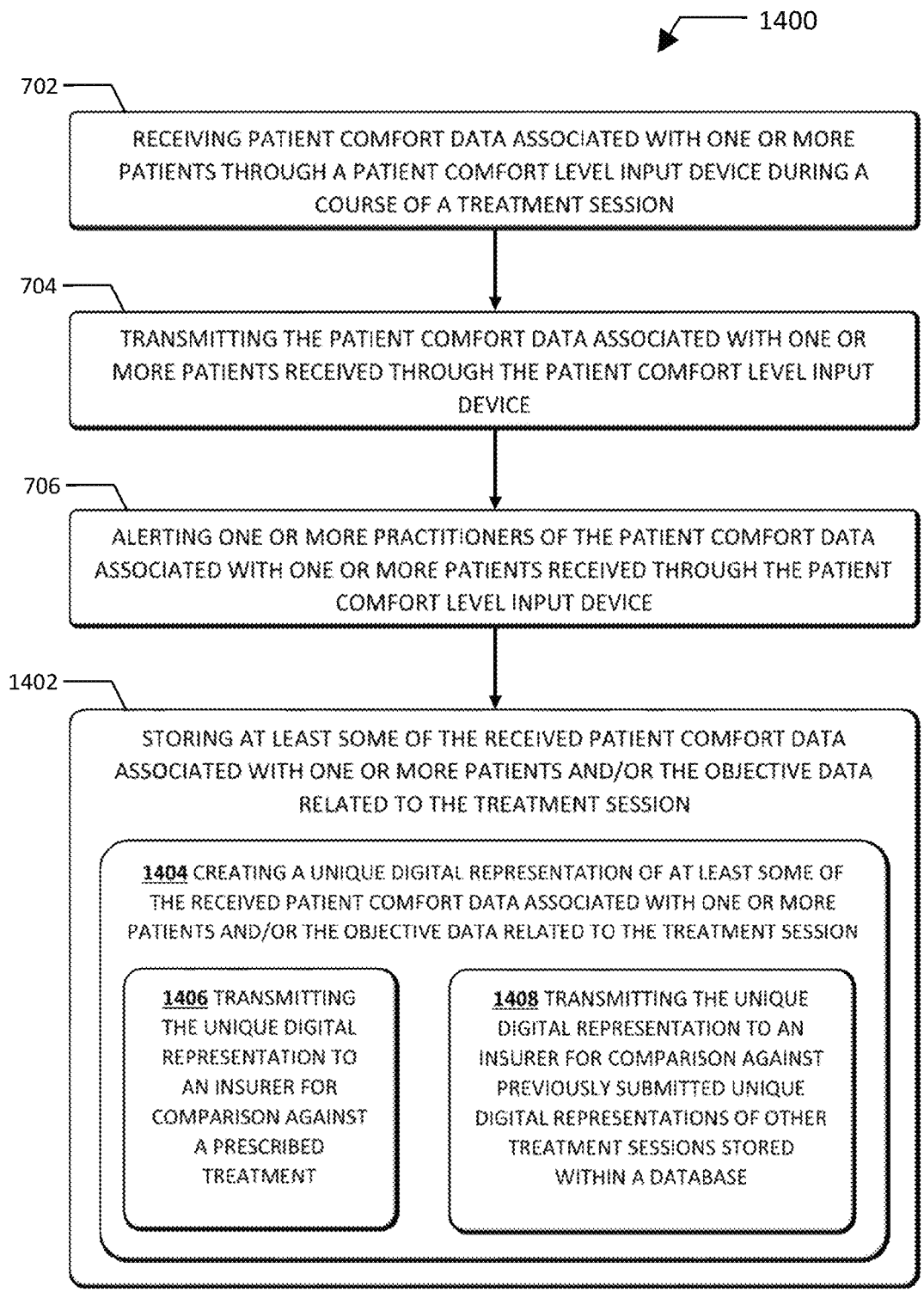

With reference to FIG. 14, in at least some implementations, in addition to operations at 702, 704, and 706 as described supra, the method may further include storing at least some of the received patient comfort data associated with one or more patients and/or the objective data related to the treatment session at 1402. For example, in some implementations, at least some feedback received from the patient during a treatment session regarding a comfort level and at least some data received from the practitioner during the course of the treatment session may be stored within a storage component of the tablet PC 602 (e.g. a solid-state drive or other data storage device) and further copied to the practice database 108 via the LAN data link 110. As depicted in FIG. 6b, in some implementations, stored data may later accessed and displayed (e.g. on GUI 600) in the form of a chart 652 which displays both objective data and 656, 658 in graphical form. In some implementations, storing at least some of the received patient comfort data associated with one or more patients and/or the objective data related to the treatment session at 1402 may include creating a unique digital representation of at least some of the received patient comfort data associated with one or more patients and/or the objective data related to the treatment session at 1404. For example, a unique digital representation of one or more specific treatment sessions may be created. This may be accomplished through storage of the precise duration of the treatment session (e.g. time between practitioner taping "Begin Session" and "End Session") as well as the precise times during the session at which various objective data and subjective data are received during the session. With reference to FIG. 6b, and more particularly, the graphical indications of subjective data related to the treatment session treatment session on Sep. 21, 2014 is visibly different than the graphical indications of that related to the session on Oct. 3, 2014. It should be appreciated that such data is represented digitally and that, due to the near impossibility that any two treatment sessions would be digitally indistinguishable, such digital representations are unique. In some implementations, the unique digital representations of particular treatment sessions are created by storing an amount of un-editable base information related to the session such as a unique treatment session docket number. In some implementations, creating a unique digital representation of at least some of the received patient comfort data associated with one or more patients and/or the objective data related to the treatment session at 1404 may include transmitting the unique digital representation to an insurer for comparison against a prescribed treatment at 1406. For example, a particular insurance policy may cover a certain number of massage appointments annually as preventive care; however, such coverage may be limited to certain types and/or specially exclude other types of massage. Accordingly, in some implementations, a unique digital representation of a treatment session indicating a type of therapy performed may be transmitted to an insurer to confirm that treatment performed matches that which the policy covers, or that the treatment matches the prescription given by the attending physician. In some implementations, creating a unique digital representation of at least some of the received patient comfort data associated with one or more patients and/or the objective data related to the treatment session at 1404 may include transmitting the unique digital representation to an insurer for comparison against previously submitted unique digital representations of other treatment sessions stored within a database at 1408. For example, an insurer may require practitioners seeking compensation for services performed to submit a unique digital representation of each and every treatment session for which insurer compensation is sought and, once transmitted to the insurer 122, the insurer 122 may compare the received unique digital representations against other unique digital representations of other treatment sessions for which reimbursement has been sought and/or paid out. One skilled in the art will understand that submission of fraudulent claims, and receipt of payout for services not performed, by some practitioners has been a longstanding and prevalent problem in many industries. Accordingly, it should be appreciated that requiring submission of a unique digital representation as a prerequisite for compensation for services purportedly performed will have the positive effect of reducing the amount of fraudulent claims received and/or paid out for and, ultimately, may reduce the cost to insurance companies leading to lower premiums. Alternatively, an insurer may offer discounted rates as in incentive, as opposed to strictly mandating use, to those whom adopt such a system of operation 1408.

Figure 15:
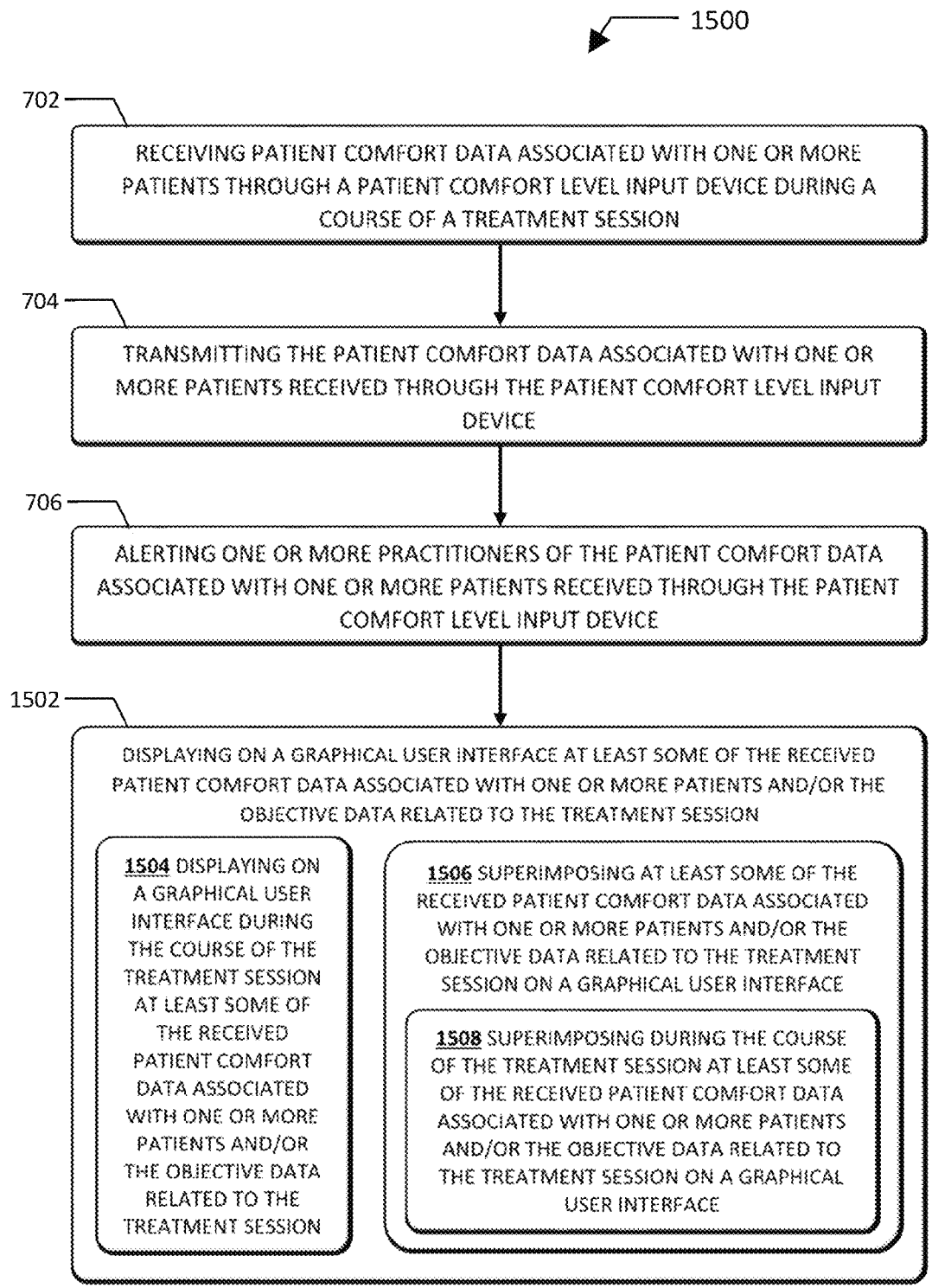

With reference to FIG. 15, in at least some implementations, in addition to operations at 702, 704, and 706 as described supra, the method may further include displaying on a graphical user interface at least some of the received patient comfort data associated with one or more patients and/or the objective data related to the treatment session at 1502. For example, various data may be displayed on GUI 600 or GUI 650 as described throughout this detailed description. In some implementations, displaying on a graphical user interface at least some of the received patient comfort data associated with one or more patients and/or the objective data related to the treatment session at 1502 may include displaying on a graphical user interface during the course of the treatment session at least some of the received patient comfort data associated with one or more patients and/or the objective data related to the treatment session at 1504. For example, in some implementations, the patient comfort data received via the patient comfort level input device 200 may be graphed onto chart 652 contemporaneously as the data is received thereby allowing the practitioner to graphically view the entirety of patient comfort data both currently being indicated and previously indicated. In some implementations, the displaying operation at 1502 may further include superimposing at least some of the received patient comfort data associated with one or more patients and/or the objective data related to the treatment session on a graphical user interface at 1506. For example and in reference to FIG. 6b, subjective data 656 from the $1^{st}$ Session on Sep. 21, 2014 is shown as superimposed onto the same chart 652 as subjective data 658 from the $2^{nd}$ Session on Oct. 3, 2014. As discussed in relation to FIG. 6b supra, such an implementation allows for progress or lack thereof to be graphically viewed by patient and practitioner making digesting/interpreting the received subjective data faster and more intuitive. In some implementations, the superimposing operation at 1506 may further include superimposing during the course of the treatment session at least some of the received patient comfort data associated with one or more patients and/or the objective data related to the treatment session on a graphical user interface at 1508. For example, GUI 650 may be set up for display during the course of the $2^{nd}$ Session on Oct. 3, 2014 while simultaneously displaying on chart 652 subjective and/or data associated with the $1^{st}$ Session. It should be appreciated that such an implementation would enable a practitioner to be alerted during the course of treatment that the patient is indicating more or less pain during a subsequent session than was previously indicated.

Figure 16:
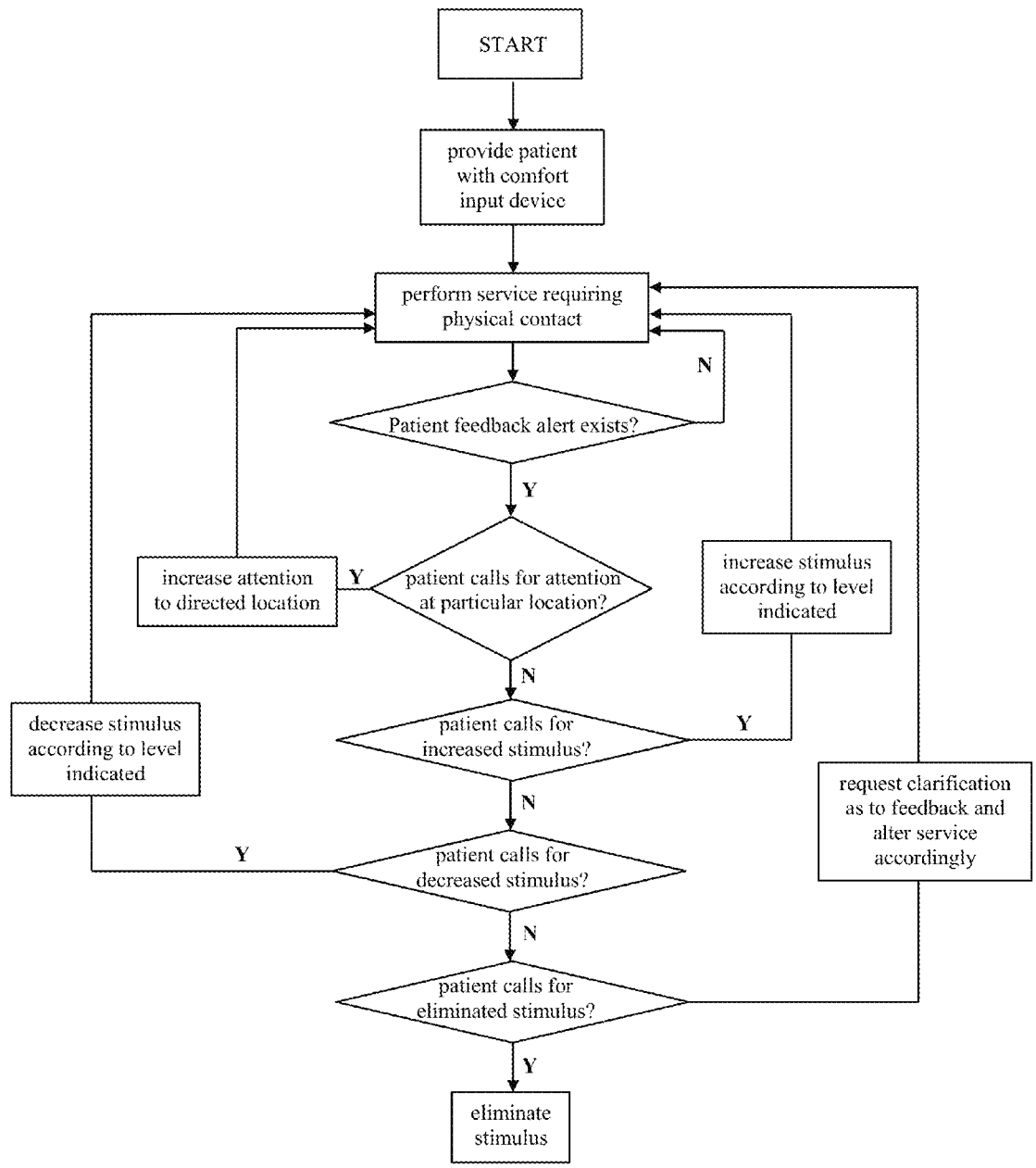
FIG. 16 is a flowchart illustrating an example of a method of incorporating nonverbally received patient comfort data or patient feedback into the performance of a service requiring physical contact.

FIG. 16 is a flowchart illustrating an example of a method of incorporating nonverbally received patient comfort data or patient feedback into the performance of a service requiring physical contact. In some embodiments, the first step of the method is to provide a patient with a patient comfort level input device. Of course if the patient is unfamiliar with the device or method then it will be necessary to explain to the patient how to use the device and any other relevant information such as, for example, how the practitioner will respond to various inputs from the patient. Assuming the practitioner has already completed whatever steps are necessary to receive the patient feedback, such as for example putting on the headset-type practitioner alerting device of FIG. 3, then the practitioner may begin performing the service requiring physical contact (e.g. massage or dentistry or physical therapy or chiropractic treatment) once the patient understands how to use the device. During the time the service is being performed the practitioner continually monitors for any patient feedback alerts; of course, such monitoring may be passive since the alerting device may attract the practitioner's attention if patient comfort data is received. If no patient feedback exists then the practitioner simply continues to perform the service requiring physical contact. However, if patient feedback exists then the practitioner must determine how the patient is calling for the practitioner to alter the service being performed.

In some embodiments, the practitioner must determine whether the patient is calling for the practitioner to increase the given attention to a particular location. For example, if the service being rendered is a therapeutic massage and the practitioner begins massaging an area where the patient has been experiencing muscle spasms and tightness, or an area with knots has developed, the patient may call for the practitioner to dedicate extra attention (e.g. time allotted during the session) as well as detail to this area. In some embodiments, the patient makes a demand by depressing a button on the patient comfort level input device 200 of FIG. 1 (a button which calls for added focus on the current particular area being treated thereby causing the speakers to sound the phrase "right there" or "that's the spot").

In some embodiments, the practitioner must determine whether the patient is calling for the practitioner to increase the amount of stimulus, e.g. the amount of pressure being applied by a massage therapist. If patient feedback exists and is calling for increased stimulus the practitioner must determine the level of increase called for and then increase the stimulus according to that level. This level may be indicated by the color of a light illuminated within the field of view of the practitioner or by the intensity at which a device is vibrating, or audio indication such as described in relation to practitioner alerting device 200.

In some embodiments, the practitioner must determine whether the patient is calling for the practitioner to decrease the amount of stimulus being induced, e.g. the amount of pressure applied in a massage or the aggressiveness with which a dental practitioner is cleaning under the patient's gum-line. If patient feedback exists and is calling for decreased stimulus the practitioner must determine the level of decrease called for and then decrease the stimulus according to that level. This level may be indicated by the color of a light illuminated within the field of view of the practitioner or by the intensity at which a device is vibrating, or audio indication such as described in relation to practitioner alerting device 200.

In some embodiments, the patient may also call for the stimulus to be eliminated altogether and, accordingly, the practitioner must also monitor the patient feedback for such a demand. In these embodiments, if the patient is calling for eliminated stimulus the practitioner will immediately stop performing the service altogether. If patient feedback exists but in a form which has not been assigned a predetermined meaning, the practitioner will pause performing the service and request clarification as to the feedback and alter the service accordingly. For example, in a particular setting the patient may be using a device with three push buttons, A, B, and C, wherein A has been assigned as calling for the practitioner to dedicate particular attention to the area currently being stimulated and B has been assigned as calling for the practitioner to eliminate the stimulus but C is assigned no meaning, i.e. it is simply an unused channel of communication. In the event that the patient depresses C the practitioner may be alerted of this selection but will be unable to know exactly what the patient is calling for. Thus, the practitioner will request clarification.

As illustrated in FIG. 16, the method is a continuous method of contemporaneously responding to patient feedback. Accordingly, all actions with the exception of eliminating stimulus generally altogether loop back to the performing service requiring physical contact step.

With regard to the particular meaning of the terms "patient" and "practitioner" as used herein, this term is intended to encompass the traditional notion of a patient in a patient-practitioner relationship (e.g. a person hiring a medical or dental or massage or other professionally licensed individual to provide a particular service). However, the term "patient" is also intended to encompass a person whom is experiencing direct or indirect physical contact with a person other than a licensed professional providing a service, and the term "practitioner" is also intended to encompass a person whom is performing a service requiring physical contact despite not being a licensed professional. For example, in an instance wherein a husband is performing a massage on his wife the husband may aptly be characterized as a practitioner, despite not being licensed as such by a governing body and furthermore the wife may be aptly characterized as a patient despite not being treated by the husband in a traditional practitioner-patient relationship. Moreover, any other type of physical contact between persons wherein it would potentially be beneficial to communicate comfort data nonverbally is within the scope of the presently disclosed and claimed system and methods for nonverbally communicating patient comfort data. For example, the system and method may be useful within private confines for use in an intimate setting to direct an intimate partner that increased/decreased stimulus is desired. Moreover, while the systems and methods herein are described with regard to exemplary settings wherein physical contact is required to perform the service, it should be appreciated that other uses which do not require physical contact are also within the scope of the methods and systems disclosed herein. For example, in some implementations a patient may be a victim of prior physical or sexual abuse and the practitioner may be a therapist assisting the patient in coping with his/her experiences such as by moving a hand incrementally closer to the patient (although not within physical contact) during which time the patient indicates through the patient comfort level input device a level of psychological (as opposed to physiological) comfort and/or discomfort. Another possible implementation is assisting a patient in management of phobias, such as for example arachnophobia or coulrophobia, wherein a spider or clown is moved incrementally closer to or farther away from a patient by a practitioner in response to psychological patient comfort data received at the patient comfort level input device.

With regard to the particular meaning of the term "physical practitioner contact" as used herein, this term is intended to encompass both direct physical contact such as a practitioner touching a patient's body (including through clothing articles) with the practitioner's hands or a tool being held by the practitioner (e.g. a powered massage machine held on muscle insertion points by a chiropractor) or a tool under the control of a practitioner whether or not being held by the practitioner (e.g. a hydrotherapy massage table the intensity of which a practitioner controls).

The foregoing description details certain implementations of the systems, devices, and methods disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the implementations. It will also be appreciated by those of skill in the art that parts included in one implementation are interchangeable with other implementations; one or more parts from a depicted implementation may be included with other depicted implementations in any combination. For example, any of the various components described herein and/or depicted in the Figures may be combined, interchanged or excluded from other implementations.

Insofar as the description above and the accompanying drawing disclose any additional subject matter that is not within the scope of the single claim below, the inventions are not dedicated to the public and the right to file one or more applications to claim such additional inventions is reserved. It is intended that any such material will be claimed in one or more applications which claim the benefit of priority from this application.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and implementations of the present development. This development is susceptible to modifications in the methods and implementations, as well as alterations in the fabrication methods and equipment. Such modifications will become apparent to those skilled in the art from a consideration of this disclosure or practice of the development disclosed herein. Consequently, it is not intended that this development be limited to the specific implementations disclosed herein, but that it cover all modifications and alternatives coming within the true scope and spirit of the development as embodied in the attached claims.

What is claimed is:

1. A system for enabling non-verbal communication between a patient and a practitioner, the system comprising:
a hand-held input device for use by the patient, the hand-held input device including at least:
a housing,
a thumb joystick that is displaceable along a channel of the housing from a center position to define comfort data, the comfort data being defined based at least partly on a distance of displacement and a direction of displacement of the thumb joystick along the channel of the housing from the center position,
a hand-held input device vibratory intensity indicator configured to vibrate the hand-held input device at an intensity that is based on the comfort data, and
a transmitter configured to transmit the comfort data; and
a headset that is wearable by the practitioner, the headset including at least:
a head-band including a first end portion and a second end portion that rest against opposing temples of the practitioner when the headset is worn,
a receiver configured to receive the comfort data,
an extension member that extends from the head-band and that includes a display indicator that is positionable within a peripheral field of view of the practitioner when the headset is worn, which display indicator is configured to display a color that is based on the comfort data, and
a headset vibratory intensity indicator that is included on the first end portion or the second end portion of the head-band and that is configured to vibrate at an intensity that is based on the comfort data.

2. The system of claim 1, wherein the thumb joystick is displaceable along the channel of the housing to one or more predefined positions to indicate (i) comfort or discomfort based on a direction of displacement and (ii) a level of comfort or discomfort based on a distance of displacement.

3. The system of claim 1, wherein the thumb joystick is displaceable along the channel of the housing to any of (i) a first comfort-indicating position to indicate a first level of comfort, (ii) a second comfort-indicating position to indicate a second level of comfort, (iii) a first discomfort-indicating position to indicate a first level of discomfort, or (iv) a second discomfort-indicating position to indicate a second level of discomfort and wherein each of the first level of comfort, the second level of comfort, the first level of discomfort, and the second level of discomfort correspond to a color that is displayable from the display indicator of the headset and an intensity of vibration that is emitted from the hand-held input device vibratory intensity indicator and the headset vibratory intensity indicator.

4. The system of claim 1, wherein the thumb joystick includes a 360 degree range of motion to indicate relative direction.

5. The system of claim 1, wherein the hand-held input device further includes an adjustable strap to secure the hand-held input device to one or more fingers of the patient.

6. The system of claim 1, wherein the hand-held input device further includes a button configured to trigger an alert event.

7. The system of claim 1, wherein the hand-held input device further includes a button configured to trigger a pre-defined command.

8. The system of claim 1, wherein the hand-held input device further includes a display to display a color that is based on the comfort data.

9. The system of claim 1, wherein the comfort data includes (i) an indication of comfort or discomfort and (ii) a level of comfort or discomfort.

10. The system of claim 1, wherein the headset-type alerting device further includes a speaker configured to output sound based on the comfort data.

11. The system of claim 1, further comprising:
a first arm-wearable device with a first vibratory intensity indicator configured to vibrate in response to an indication of comfort received from the hand-held input device; and
a second arm-wearable device with a second vibratory intensity indicator configured to vibrate in response to an indication of discomfort received from the hand-held input device.

12. The system of claim 1, further comprising:
an illumination alerting device configured to illuminate with a color that is based on the comfort data transmitted from the hand-held input device.

13. The system of claim 1, wherein the thumb joystick is displaceable along a channel of the housing to one or more predefined positions to indicate a positive indication or a negative indication.

14. The system of claim 1, wherein the head-band further includes a second headset vibratory intensity indicator that is included on the first end portion or the second end portion of the head-band opposite the first headset vibratory intensity indicator, wherein the first headset vibratory intensity indicator is configured to vibrate against a first temple of the practitioner at an intensity that is based on a level of comfort, and wherein the second headset vibratory intensity indicator is configured to vibrate against a second temple of the practitioner at an intensity that is based on a level of discomfort.

15. The system of claim 1, wherein the thumb joystick is displaceable along the channel of the housing from a center position to indicate a request for an amount of increased pressure, the amount of increased pressure being defined based at least partly on a distance of displacement of the thumb joystick along the channel of the housing from the center position in a first specified direction, wherein the headset vibratory intensity indicator is configured to vibrate at an intensity that is based on the amount of increased pressure, and wherein the display indicator is configured to display a single color that is based on the amount of increased pressure.

* * * * *